United States Patent [19]
Panayotatos

[11] Patent Number: 5,846,935
[45] Date of Patent: Dec. 8, 1998

[54] MODIFIED CILIARY NEUROTROPHIC FACTORS

[75] Inventor: Nikos Panayotatos, Orangeburg, N.Y.

[73] Assignee: Regeneron Pharmaceuticals, Inc., Tarrytown, N.Y.

[21] Appl. No.: 308,736

[22] Filed: Sep. 19, 1994

Related U.S. Application Data

[63] Continuation-in-part of Ser. No. 959,284, Oct. 9, 1992, Pat. No. 5,349,056.
[51] Int. Cl.⁶ .............................. A61K 38/18; C07K 14/48
[52] U.S. Cl. .............................. 514/12; 530/399; 930/120
[58] Field of Search ..................................... 530/399, 350; 930/10, 120; 514/12

[56] References Cited

U.S. PATENT DOCUMENTS

| | | | |
|---|---|---|---|
| 4,959,314 | 9/1990 | Mark et al. | 435/69.1 |
| 4,997,929 | 3/1991 | Collins et al. | 536/27 |
| 5,593,857 | 1/1997 | Higaki | 435/69.1 |

FOREIGN PATENT DOCUMENTS

| | | |
|---|---|---|
| 0 446 931 A 1 | 9/1991 | European Pat. Off. . |
| WO 93/02206 | 2/1993 | WIPO . |

OTHER PUBLICATIONS

Panayotatos et al. J. Biol. Chem. 268(1993): 19000–19003.
Cunningham et al. Science 244(1989): 1081–1085.
Masiakowski, et al., Recombinant Human and Rat Ciliary Neurotrophic Factors, J. Neurochemistry 57:1003–1012 (1991).
Lin, et al., Purification, Cloning and Expression of Ciliary Neurotrophic Factor, Science 246: 1023–1025 (1989).
Alber, T., Mutational Effects on Protein Stability, Annu. Rev. Biochem. 58: 765–798 (1989).

*Primary Examiner*—Marianne P. Allen
*Assistant Examiner*—Robert C. Hayes
*Attorney, Agent, or Firm*—Gail M. Kempler; Robert J. Cobert

[57] ABSTRACT

Modified ciliary neurotrophic factors and methods for their production and therapeutic use. Also described is a method of screening for novel therapeutic proteins by determining altered electrophoretic binding properties.

14 Claims, 15 Drawing Sheets

Fig. 1A

```
              Nhe1                          AlwN1                              Hind3
         10         20         30         40         50         60         70         80         90        100
MAFTEHSPLTPHRRDLCSRSIWLARKIRSDLTALTESYVKHQGLNKNINLDSADGMPVASTDQWSELTEAERLQENLQAYRTFHVLLARLLEDQQVHFTP
hu  ....A.QT..L......................M............................V..V......R..M.....................QGM.TK......R....
rt  ...M..A.........E....T..........................................V..V.M......................IM.................
rb  ....A.Q..L............................................M.....S.V..........R..M..................-QGMLT..........R....
ms  ..AADTPSA.LRHH......G.R....M....V.D.LDI..ER....DAS.SVAAV..V.T.AVER.A.Q.GTQ..LD..A...A.RT...QM..E.RELLGD
ch 186 .....A.QT..L......................M.............................V..V......R..M.....................QGM.TK...........
187
188 .....A.QT..L......................M.............................V..V......R..M.....................QGM.TK......R....
189                                     M                              V  V     R  M                   QGM TK      R
192                                                                    V  V     R  M
218                                                                    V  V     R  M
219                                                                    V        R  M
222                                                                    V        R  M
223                                                                    V        R  M
228                                                                             R 10         20         30         40         50         60         70         80         90        100
```

Fig. 1B

```
             110       120       130       140       150       160       170       180       190       200
hu    TEGDFHQAIHTLLLQVAAFAYQIEELMILLEYKIPRNEADGMPINVGDGGLFEKKLWGLKVLQELSQWTVRSIHDLRFISSHQTGIPARGSHYIANNKKM
rt    ....M..S.........L...V...Q...E......AT..................H..................V....M..S.LE...G.KD.Q.
rb    A...HF...........V...CN..PKD..T.V-I.GD......................................V..C....H.........D.E.
ms    ........T-..S....A...Q.-V...VTI.............................................V...HM..S.H-...G...-Q
ch    .DAELGP.LAAM....S..V.HL..LE-..SRGAPA.EGSE.PAPPRLS...Q..R..R..R..A..A....VR....QL.K.G---.GS.AALGLPESQ-

Bsa1                                      BamH1

CAATCCCATTAGTAGAGAATGCCAGTGGGTTTAGTCTTTGAGAGTCACATCTCTTATTTG

GACCAGTATAGACAGAAGTAAACCCAGCTGACTTGTTCCTGGACAGTTGAGTTAAGGG

```
 M  A  E  H  S  P  L  T  P  H  R  R  D  L  C  S  R  S
ATGGCTTTCACAGAGCATTCACCGCTGACCCCTCACCGTCGGGACCTCTGTAGCCGCTCT

I  W  L  A  R  K  I  R  S  D  L  T  A  L  T  E  S  Y  V  K
ATCTGGCTAGCAAGGAAGATTCGTTCAGACCTGACTGCTCTTACGGAATCCTATGTGAAG

H  Q  G  L  N  K  N  I  N  L  D  S  A  D  G  M  P  V  A  S
CATCAGGGCCTGAACAAGAACATCAACCTGGACTCTGCGGATGGGATGCCAGTGGCAAGC

T  D  Q  W  S  E  L  T  E  A  E  R  L  Q  E  N  L  Q  A  Y
ACTGATCAGTGGAGTGAGCTGACCGAGGCAGACTCCAAGAGAACCTTCAAGCTTAT
```

GTGCA

Fig. 13B

```
  R   T   F   H   V   L   L   A   R   L   L   E   D   Q   Q   V   H   F   T   P
CGTACCTTCCATGTTTTGTTGGCCAGGCTCTTAGAAGACCAGCAGGTGCATTTTACCCCA

T   E   G   D   F   H   Q   A   I   H   T   L   L   L   Q   V   A   F   E   A
ACCGAAGGTGACTTCCATCAAGCTATACATACCCTTCTTCTCCAAGTCGCTGCCTTTGCA

Y   Q   I   E   E   L   M   I   L   L   E   Y   K   I   P   R   N   E   A   D
TACCAGATAGAGGAGTTAATGATACTCCTGGAATACAAGATCCCCGCAATGAGGCTGAT

G   M   P   I   N   V   G   D   G   G   L   F   E   K   K   L   W   G   L   K
GGGATGCCTATTAATGTTGGAGATGGTGGTCTCTTTGAGAAGAAGCTGTGGGGCCTAAAG

V   L   Q   E   L   S   Q   W   T   V   R   S   I   H   D   L   R   F   I   S
GTGCTGCAGGAGCTTTCACAGTGGACAGTAAGGTCCATGACCTTCGTTTCATTTCT

S   H   Q   T   G   I   P   A   R   G   S   H   Y   I   A   N   N   K   K   M
TCTCATCAGACTGGGATCCCAGCACGTGGGAGCCATTATATTGCTAACAACAAGAAAATG

TAGCAGTTAGTCCCTTCTCTCTCTTACTTTCTCTTCTAATGGAATATGCGTAGTT
```

MODIFIED CILIARY NEUROTROPHIC FACTORS

This application is a continuation-in-part of U.S. Ser. No. 07/959,284 filed Oct. 9, 1992, now U.S. Pat. No. 5,349,056 issued Sep. 20, 1994.

BACKGROUND OF THE INVENTION

The present invention relates to therapeutic CNTF-related poly-peptides useful for the treatment of neurological or other diseases or disorders.

Ciliary neurotrophic factor (CNTF) is a protein that is required for the survival of embryonic chick ciliary ganglion neurons in vitro (Manthorpe et al.,1980, J. Neurochem. 34:69–75). The ciliary ganglion is anatomically located within the orbital cavity, lying between the lateral rectus and the sheath of the optic nerve; it receives parasympathetic nerve fibers from the oculomotor nerve which innervates the ciliary muscle and sphincter pupillae.

Over the past decade, a number of biological effects have been ascribed to CNTF in addition to its ability to support the survival of ciliary ganglion neurons. CNTF is believed to induce the differentiation of bipotential glial progenitor cells in the perinatal rat optic nerve and brain (Hughes et al., 1988, Nature 335:70–73). Furthermore, it has been observed to promote the survival of embryonic chick dorsal root ganglion sensory neurons (Skaper and Varon, 1986, Brain Res. 389:39–46). In addition, CNTF supports the survival and differentiation of motor neurons, hippocampal neurons and presympathetic spinal cord neurons [Sendtner, et al., 1990, Nature 345:440–441; Ip, et al. 1991, J. Neurosci. 11:3124–3134; Blottner, et al. 1989, Neurosci. Lett. 105:316–320].

It has long been known that innervation of skeletal muscle plays a critical role in the maintenance of muscle structure and function. Skeletal muscle has been shown recently to be a target of positive CNTF actions. Specifically, CNTF prevents both the denervation-induced atrophy (decreased wet weight and myofiber cross sectional area) of skeletal muscle and the reduced twitch and tetanic tensions of denervated skeletal muscle (Helgren et al., Cell 76:493–504 (1994)). In this model, human CNTF also produces an adverse effect that is manifested as a retardation of weight gain. This adverse effect has also been observed in clinical trials with rHCNTF for the treatment of ALS. Therefore, simultaneous measurements of muscle weight and animal body weight following denervation could be used as a measure of efficacy and adverse reaction, respectively, in response to treatment with rHCNTF or other compounds. The ratio of the potency values obtained from these measurements is defined as the therapeutic index (T.I.), expressed here as $TD_{25}/ED_{50}$, so that the higher the value of T.I., the safer the compound at a therapeutic dose.

CNTF has been cloned and synthesized in bacterial expression systems, as described by Masiakowski, et al., 1991, J. Neurosci. 57:1003–1012 and in International Publication No. WO 91/04316, published on Apr. 4, 1991, which are incorporated by reference in their entirety herein.

The receptor for CNTF (termed "CNTFRα") has been cloned, sequenced and expressed [see Davis, et al. (1991) Science 253:59–63]. CNTF and the haemopoetic factor known as leukemia inhibitory factor (LIF) act on neuronal cells via a shared signaling pathway that involves the IL-6 signal transducing component gp130 as well as a second, β-component (know as LIFR β); accordingly, the CNTF/CNTF receptor complex can initiate signal transduction in LIF responsive cells, or other cells which carry the gp130 and LIFRβ components [Ip, et al. (1992) Cell 69:1121–1132].

In addition to human CNTF, the corresponding rat (Stöckli et al., 1989, Nature 342:920–923), and rabbit (Lin et al., 1989, J. Biol. Chem. 265:8942–8947) genes have been cloned and found to encode a protein of 200 amino acids, which share about 80% sequence identity with the human gene. Both the human and rat recombinant proteins have been expressed at exceptionally high levels (up to 70% of total protein) and purified to near homogeneity.

Despite their structural and functional similarity, recombinant human and rat CNTF differ in several respects. The biological activity of recombinant rat CNTF in supporting survival and neurite outgrowth from embryonic chick ciliary neurons in culture is four times better than that of recombinant human CNTF [Masiakowski et al., (1991), J. Neurochem. 57:1003–1012]. Further, rat CNTF has a higher affinity for the human CNTF receptor than does human CNTF.

A surprising difference in the physical properties of human and rat CNTF, which are identical in size, is their different mobility on SDS gels. This difference in behaviour suggests the presence of an unusual structural feature in one of the two molecules that persists even in the denatured state (Masiakowski et al., 1991, id.).

Mutagenesis by genetic engineering has been used extensively in order to elucidate the structural organization of functional domains of recombinant proteins. Several different approaches have been described in the literature for carrying out deletion or substitution mutagenesis. The most successful appear to be alanine scanning mutagenesis [Cunningham and Wells (1989), Science 244:1081–1085] and-homolog-scanning mutagenesis [Cunningham et al., (1989), Science 243:1330–1336]. These approaches helped identify the receptor binding domains of growth hormone and create hybrid proteins with altered binding properties to their cognate receptors.

To better understand the physical, biochemical and pharmacological properties of rHCNTF, applicant undertook rational mutagenesis of the human and rat CNTF genes based on the different biological and physical properties of their corresponding recombinant proteins (See Masiakowski, P., et al. (1991) J. Neurochem., 57, 1003–1012). Applicant has found that the nature of the amino acid at position 63 could greatly enhance the affinity of human CNTF for sCNTFRα and its biological potency in vitro (Panayotatos, N., et al. , J. Biol. Chem., 268, 19,000–19,003 (1993); Panayotatos, N., et al., Biochemistry, 33, 5813–5818 (1994).

SUMMARY OF THE INVENTION

An object of the present invention is to provide novel CTNF-related neurotrophic factors for the treatment of diseases or disorders including, but not limited to, motor neuron diseases and muscle degenerative diseases.

A further object of the present invention is to provide a method for identifying CNTF-related factors, other than those specifically described herein, that have improved therapeutic properties.

These and other objects are achieved in accordance with the invention, whereby amino acid substitutions in human CNTF protein enhance its therapeutic properties. In one embodiment, alterations in electrophoretic mobility are used to initially screen potentially useful modified CNTF proteins.

In a preferred embodiment, the amino acid glutamine in position 63 of human CNTF is replaced with arginine (referred to as 63QR) or another amino acid which results in a modified CNTF molecule with improved biological activity. In further embodiments, rHCNTF variants combine the 63QR mutation with three other novel features:

1) Deletion of the last 13 amino acid residues (referred to as ΔC13) to confer greater solubility to rHCNTF without impairing its activity;
2) Substitution of the unique cysteine residue at position 17, which results in stabilization of rHCNTF in physiological buffer, at physiological pH and temperature conditions without affecting its activity; or
3) Substitution of amino acid residue 64W, which alters the biological activity of rHCNTF in vitro and which results in a 7-fold improvement of its therapeutic index in vivo.

In another preferred embodiment, a molecule designated RG297 (rHCNTF,17CA63QRΔC13) combines a 63QR substitution (which confers greater biological potency) with a deletion of the terminal 13 amino acid residues (which confers greater solubility under physiological conditions) and a 17CA substitution (which confers stability, particularly under physiological conditions at 37° C.) and shows a 2–3 fold better therapeutic index than rHCNTF in an animal model.

In another preferred embodiment, a molecule designated RG242 is described that carries the double substitution 63QR64WA which results in a different spectrum of biological potency and a 7-fold higher therapeutic index.

In another preferred embodiment, a molecule designated RG290 is described that carries the double substitution 63QRΔC13 which confers greater solubility under physiological conditions.

BRIEF DESCRIPTION OF THE DRAWINGS

FIGS. 1A–B—Alignment of CNTF protein sequences. Human (SEQ ID NO:1), rat (SEQ ID NO:2), rabbit (SEQ ID NO:3) mouse (SEQ ID NO:4) and chicken (SEQ ID NO:5) (Leung, et al., 1992, Neuron 8:1045–1053) sequences. Dots indicate residues found in the human sequence. Modified CNTF molecules (186 [SEQ ID NO: 6], 187 [SEQ ID NO: 7], 188 [SEQ ID NO: 8], 189 [SEQ ID NO: 9], 192 [SEQ ID NO. 10], 218[SEQ ID NO: 11], 219 [SEQ ID NO: 12], 222 [SEQ ID NO: 13], 223 [SEQ ID NO: 14] and 228 [SEQ ID NO:15 ] showing human CNTF amino acid residues (dots) and rat CNTF (residues shown). The name of the purified recombinant protein corresponding to each sequence is shown on the left.

FIG. 3B. human CNTF (filled diamonds), rat CNTF (open squares), and RPN228 (filled squares). Dose response of dissociated E8 chick ciliary neurons surviving at the indicated protein concentration, as a percentage of the number of neurons surviving in the presence of 2 ng/ml rat CNTF. Each experimental point represents the mean of three determinations.

(FIG. 11B) hCNTF vs. RG297 and (FIG 11C) hCNTF vs. RG242.

FIGS. 13A–13B—Sequence of Human CNTF. Human nucleic acid (SEQ ID No. 20) and amino acid (SEQ ID No. 21) sequences.

DETAILED DESCRIPTION OF THE INVENTION

Figure 2:
FIG. 2—Mobility of human, rat and several modified CNTF molecules on reducing SDS-15% polyacrylamide gels. Purified recombinant proteins were loaded as indicated. Markers of the indicated MW were loaded on lane M.

The present invention relates to a method of treating neurological diseases and disorders in humans or animals. It is based, in part, on the initial finding that recombinant rat CNTF binds more efficiently to the human CNTF receptor than does recombinant human CNTF and the subsequent discovery that amino acid substitutions which cause human CNTF to more closely resemble rat CNTF result in enhanced binding of the modified CNTF to the human CNTF receptor and concomitant enhanced biological activity.

In a preferred embodiment, alteration of a single amino acid of the human CNTF protein results in a significant enhancement of the ability of the protein to promote the survival and outgrowth of ciliary ganglion neurons.

Recombinant human and rat CNTF have the same number of amino acids (199) and similar mass (MW 22,798 and 22,721 respectively, 20 after removal of the N-terminal methionine). Yet, on reducing SDS-PAGE gels, recombinant human CNTF migrates as a protein of MW=27,500, whereas rat CNTF migrates with the expected mobility. In addition, human CNTF has four times lower biological activity towards chick ciliary ganglion (CG) neurons than rat CNTF and the human protein competes for binding to the human or the rat receptor on cell surfaces much less effectively than rat CNTF.

The above observation led to a directed effort to identify the region on the CNTF molecule responsible for these differences. This method involved the exchange, by genetic engineering methods, of parts of the human CNTF sequence with the corresponding rat CNTF sequence and vice versa. To achieve this, advantage was taken of restriction sites that are common to the two CNTF genes and unique in their corresponding expression vectors. When necessary, such sites were engineered in one or the other of the two genes in areas that encode the same protein sequence. With this approach, expression vectors were obtained for each of the modified proteins shown in FIGS. 1A & 1B. After isolating the individual proteins to at least 60% purity, their properties, as compared to those of human and rat CNTF were determined.

Because the electrophoretic mobilities of human and rat CNTF differ significantly, the effect of each amino acid substitution was monitored initially by making a determination of the effect of such change on the mobility of the protein. As described herein, electrophoretic mobility data indicated that all of the modified human CNTF molecules that migrated to the same position as rat CNTF had the single amino acid substitution Gln63→Arg (Q63→R).

Modified human CNTF proteins that demonstrated an electrophoretic mobility similar to that of the rat CNTF molecule were subsequently examined for biological activity and receptor binding.

CNTF is characterized by its capacity to support the survival of dissociated ciliary neurons of E8 chick embryos. By this criterion, purified recombinant rat CNTF is as active as the native protein from rat, but four times more active than recombinant human CNTF [Masiokowski, et al. (1991), id]. The same assay was utilized to determine the biological activity of the altered molecules prepared as described above. As described herein, all of the modified CNTF molecules that had the Q63→R substitution exhibited an increased ability to support the survival of ciliary ganglion neurons as compared to the parent human CNTF protein. Such results indicated a strong correlation between alteration of the electrophoretic mobility and enhanced biological properties.

In addition to measuring the biological effect of modifications made to human CNTF, an indication of the potential biological activity of each of the molecules may also be obtained by determining the effect of each modification on the ability of the molecules to bind to the CNTF receptor.

In one embodiment, the ability of the modified human CNTF proteins to compete with rat CNTF for binding to rat superior cervical ganglia neurons (SCGs) is measured. As described herein, human CNTF is about 90 times less potent in displacing $^{125}$I-labelled rat CNTF binding from these cells than unlabelled rat CNTF. Several of the modified human CNTF proteins described herein, however, are more potent than the human CNTF in displacing the rat protein. All of the molecules described herein that had such increased competitive binding ability were molecules that exhibited altered electrophoretic mobility, wherein the molecules migrated in a manner similar to rat CNTF.

In another embodiment, cells, such as MG87 fibroblasts, are engineered to express the human CNTF receptor α-component and such cells are used to assay the binding capability of the modified protein to the human receptor. Human CNTF is about 12 times less potent than rat CNTF in competing with $^{125}$I-labelled rat CNTF for binding to the human CNTF receptor. Several of the modified human CNTF molecules described herein, including all of those with electrophoretic mobility that resemble rat rather than human CNTF, were more potent than human CNTF in competing with binding of $^{125}$I-rat CNTF to the cells expressing the human CNTF receptor.

In another embodiment, an animal model with demonstrated utility in providing an indication of the ability of certain growth and other factors to prevent degeneration of retinal photoreceptors may be used to assess the therapeutic properties of the modified CNTF molecules according to the present invention. As described in Example 4, hCNTF (Gln63→Arg) has a ten-fold higher ability than recombinant human CNTF to prevent degeneration of photoreceptors in a light-induced damage model of retinal degeneration.

Thus, according to the invention, certain amino acid substitutions in the human CNTF protein result in modified human CNTF proteins that exhibit enhanced binding to the human CNTF receptor and therefore, would be expected to have enhanced therapeutic properties.

The modified CNTF molecules useful for practicing the present invention may be prepared by cloning and expression in a prokaryotic or eukaryotic expression system. The recombinant neurotrophin gene may be expressed and purified utilizing any number of methods. The gene encoding the factor may be subcloned into a bacterial expression vector, such as for example, but not by way of limitation, pCP110.

The recombinant factors may be purified by any technique which allows for the subsequent formation of a stable, biologically active protein. For example, and not by way of limitation, the factors may be recovered from cells either as soluble proteins or as inclusion bodies, from which they may be extracted quantitatively by 8M guanidinium hydrochloride and dialysis. In order to further purify the factors, conventional ion exchange chromatography, hydrophobic interaction chromatography, reverse phase chromatography or gel filtration may be used.

According to the present invention, modified CNTF molecules produced as described herein, or a hybrid or mutant thereof, may be used to promote differentiation, proliferation or survival in vitro or in vivo of cells that are responsive to CNTF, including cells that express receptors of the CNTF/IL-6/LIF receptor family, or any cells that express the appropriate signal transducing component, as described, for example, in Davis, et al. (1992) Cell 69:1121–1132. Mutants or hybrids may alternatively antagonize cell differentiation or survival.

The present invention may be used to treat disorders of any cell responsive to CNTF or the CNTF/CNTF receptor complex. In preferred embodiments of the invention, disorders of cells that express members of the CNTF/IL-6/LIF receptor family may be treated according to these methods. Examples of such disorders include but are not limited to those involving the following cells: leukemia cells, hematopoietic stem cells, megakaryocytes and their progenitors, DA1 cells, osteoclasts, osteoblasts, hepatocytes, adipocytes, kidney epithelial cells, embryonic stem cells, renal mesangial cells, T cells, B cells, etc.

Accordingly, the present invention provides for methods in which a patient suffering from a CNTF-related neurological or differentiation disorder or disease or nerve damage is treated with an effective amount of the modified CNTF, or a hybrid or mutant thereof. The modified CNTF molecules may be utilized to treat disorders or diseases as described for CNTF in International Publication No. WO91/04316 published on Apr. 4, 1991 by Masiakowski, et al. and for CNTF/CNTFR complex as described in International Publication No. WO91/19009 published on Dec. 12, 1991 by Davis, et al. both of which are incorporated by reference in their entirety herein.

Such diseases or disorders include degenerative diseases, such as retinal degenerations, diseases or disorders involving the spinal cord, cholinergic neurons, hippocampal neurons or diseases or disorders involving motorneurons, such as amyotrophic lateral sclerosis or those of the facial nerve, such as Bell's palsy. Other diseases or disorders that may be treated include peripheral neuropathy, Alzheimer's disease, Parkinson's disease, Huntington's chorea, or muscle atrophy resulting from, for example, denervation, chronic disuse, metabolic stress, and nutritional insufficiency or from a condition such as muscular dystrophy syndrome, congenital myopathy, inflammatory disease of muscle, toxic myopathy, nerve trauma, peripheral neuropathy, drug or toxin-induced damage, or motor neuronopathy.

The present invention also contemplates diseases or disorders resulting from damage to the nervous system, wherein such damage may be caused by trauma, surgery, infarction, infection and malignancy or by exposure to a toxic agent.

The present invention also provides for pharmaceutical compositions comprising a modified CNTF molecule or hybrid or mutant thereof, as described herein, as the sole therapeutic agent or in a complex with the CNTF receptor, in a suitable pharmacologic carrier.

The active ingredient, which may comprise the modified CNTF, stable modified CNTF/CNTF receptor complex, or a hybrid or mutant thereof, should be formulated in a suitable pharmaceutical carrier for systemic or local administration in vivo by any appropriate route including, but not limited to injection (e.g., intravenous, intraperitoneal, intramuscular, subcutaneous, endoneural, perineural, intraspinal, intraventricular, intravitreal, intrathecal etc.), by absorption through epithelial or mucocutaneous linings (e.g., oral mucosa, rectal and intestinal mucosa, etc.); or by a sustained release implant, including a cellular or tissue implant.

Depending upon the mode of administration, the active ingredient may be formulated in a liquid carrier such as saline, incorporated into liposomes, microcapsules, polymer or wax-based and controlled release preparations, or formulated into tablet, pill or capsule forms.

The concentration of the active ingredient used in the formulation will depend upon the effective dose required and the mode of administration used. The dose used should be sufficient to achieve circulating plasma concentrations of active ingredient that are efficacious. Effective doses may be extrapolated from dose-response curves derived from in vitro or animal model test systems.

As described herein, applicants have determined that altered electrophoretic mobility provides a reliable method for screening for proteins with enhanced biological activity or ligand binding capability. Accordingly, the method described herein may have general applicability in screening for novel therapeutic proteins. Such a method would involve determining the electrophoretic mobility of a wild-type human protein, introducing amino acid substitutions into the wild-type human protein and identifying as potential candidates substituted proteins that have altered electrophoretic mobility as compared to the electrophoretic mobility of the wild-type protein. Such substitute proteins could be further tested to determine their biological activity and/or binding affinity. Potential amino acid substitutions could be based, for example, on comparable sequences from homologous proteins of non-human species.

One skilled in the art will recognize that other alterations in the amino acid sequence of CNTF may provide enhanced properties to the molecule. One skilled in the art will also recognize that CNTF homologues from other species, i.e. mouse, rabbit and chicken, may also have enhanced properties in treating human diseases or disorders. Thus, the present invention contemplates a method of identifying novel neurotrophic factors, whereby neurotrophic factors from species other than human are identified and assayed with respect to their ability to bind the human receptor as well as their biological activity in human cell lines and in vivo systems. When neurotrophic factors from animal species are identified which have novel properties, methods known to those in the art, such as those described herein, can be used to interchange portions of the human factor with the animal-derived factor to create novel neurotrophic factors with enhanced therapeutic properties. Here we compare the therapeutic index of rHCNTF derivatives with the 63QR mutation and/or in combination with other structural modifications of rHCNTF.

The solubility of recombinant human CNTF (rHCNTF) is very limited in physiological buffer, e.g., Phosphate-Buffered-Saline, pH 7.4 (PBS). Furthermore, the solubility over at least the 4.5–8.0 pH range depends strongly on the temperature and on the time of incubation. At 5° C., the solubility of rHCNTF in PBS is 1 mg/ml and the solution is stable for a few hours, but at 37° C. its solubility is only 0.1 mg/ml after 2 hr and 0.05 mg/ml after 48 hrs. This limited solubility and thermal stability preclude stable formulation of rHCNTF in physiological buffer. Such formulations are particularly desirable for continuous administration through the cerebrospinal fluid (CSF).

It was discovered that rHCNTF lacking the last 13 amino acid residues from the carboxyl end (rHCNTF,ΔC13 also designated RPN160 or RG160) retains full biological activity and is soluble at low temperatures (5–10° C.) to at least 12 mg/ml. Yet, despite this far greater solubility, rHCNTF, ΔC13 still falls out of a PBS solution upon incubation at 37° C. over a period of several hours, even at concentrations as low as 0.1 mg/ml.

It was determined that the thermal instability of rHCNTF and rHCNTF,ΔC13 was the result of aggregation that was initiated by intermolecular disulfide bond formation and depended strongly on protein concentration and temperature. By replacing the single cysteine residue at position 17 of human CNTF with an alanine residue, proteins were obtained that show far greater stability and maintain their biological activity after incubation for at least 7 days in PBS at 37° C. This property is maintained in rHCNTF,63QR variants which have higher potency due to the substitution of the glutamine residue at position 63 by arginine. In a particular example, rHCNTF,17CA,63QR,ΔC13 (also designated RG297) shows greater biological potency than rHCNTF because of the 63QR substitution, greater solubility because of the ΔC13 deletion and greater stability because of the 17CA substitution.

EXAMPLES

Example 1

Electrophoretic Mobility of Modified Human GNTF Molecules

Materials and Methods
Preparation of Modified CNTF molecules
Bacterial Strains and Plasmids E. coli K-12 RFJ26 is a strain that overproduces the lactose operon repressor.

The expression vectors pRPN33, which carries the human CNTF gene and pRPN110 which carries the rat CNTF gene are nearly identical (Masiakowski, et al. 1991, id.).

Plasmid pRPN219 was constructed by first digesting pRPN33 with the restriction enzymes Nhe 1 plus Hind3 and gel purifying the 4,081 bp fragment. The second, much smaller fragment which codes for part of the human CNTF gene was subsequently replaced with an 167 bp Nhe1-Hind3 fragment that was obtained by PCR amplification from the rat gene using the primers RAT-III-dniH: 5' ACGGTAAGCT TGGAGGTTCTC 3' (SEQ ID NO:16); and RAT-Nhe-I-M: 5' TCTATCTGGIC TAGCAAGGAA GATTCGTTCA GACCTGACTG CTCTTACG 3' (SEQ ID NO:17).

Plasmid pRPN228 was constructed in the same manner as pRPN219, except that the 167 bp replacement fragment was amplified using the DNA primers Rat-III-dniH-L-R: 5' AAG GTA CGA TAA GCT TGG AGG TTC TCT TGG AGT CGC TCT GCC TCA GTC AGC TCA CTC CAM CGA TCA GTG 3' (SEQ ID NO:18) and Rat-Nhe-I: 5' TCT ATC TGG CTA GCA AGG MG 3' (SEQ ID NO:19).

Plasmids pRPN186, pRPN187, pRPN188, pRPN189, pRPN192, pRPN218, and pRPN222 were generated by similar means or by direct exchange of DNA fragments using the unique restriction sites shown in FIGS. 1A & 1B.

The identity of all plasmids was confirmed by restriction analysis and DNA sequencing.

Protein Purification

Induction of protein synthesis, selective extraction, solubilization and purification from inclusion bodies were as described for rat and human CNTF (Masiakowski, et al. 1991, id.) except that gel filtration was occasionally used instead or in addition to ion exchange chromatography. Alternatively, proteins were purified from the supernatants of cell lysates by streptomycin and ammonium sulfate fractionation, followed by column chromatography, as described for other proteins (Panayotatos et al., 1989, J. Biol. Chem. 264:15066–15069). All proteins were isolated to at least 60% purity.

Conditions for enzymatic reactions, DNA electrophoresis and other techniques used in these studies have been described in detail (Panayotatos, N. 1987, Engineering an Efficient Expression System in Plasmids: A practical Approach (Hardy, K.G. ed.) pp 163–176, IRL Press, Oxford, U.K.).

Results

The mobilities of human, rat and several chimeric CNTF molecules on reducing SDS-polyacrylamide gels are shown in FIG. 2. The chimeric molecules RPN186, RPN189, RPN218 and RPN228 exhibit mobilities comparable to rat CNTF, whereas RPN187, RPN188, RPN192 and RPN222 exhibit mobilities comparable to human CNTF. Cross-reference of these results to the aligned sequences of these proteins in FIGS. 1A & 1B reveals that all proteins carrying an arginine residue at position 63 (R63) display the mobility of rat CNTF. In the case of RPN228, this single amino acid substitution (Q63→R) is sufficient to confer to human CNTF the normal mobility of rat CNTF.

FIG. 2 also provides a measure of the purity of the different recombinant proteins. By visual inspection, purity varies from 60% for RPN189 to better than 90% for RPN228.

Example 2

Measurement of Binding Activity of Modified CNTF Molecules

Materials and Methods
Preparation of $^{125}$I-CNTF

Recombinant rat CNTF (28 µg) in 37 µl 0.2 M sodium borate buffer, pH 8.5 was transfered to a vial containing 4 mCi, (2,000 Ci/mmole; NEN) of $_{125}$I and reagent (Bolton and Hunter,1973, Biochem J. 133:529–539) which had been dried under a gentle stream of nitrogen. Reactions were incubated for 45 min at 0° C. followed by 15 min at room temperature and terminated by the addition of 30 ml of 0.2 M glycine solution. After 15 min, 0.2 ml PBS containing 0.08% gelatin was also added and the mixture was passed through a Superdex-75 column (Pharmacia) to separate the labelled monomeric CNTF from dimeric and other multimeric derivatives. Percentage of incorporation was typically 20%, as determined by thin layer chromatography and the specific activity was typically around 1,000 Ci/mmole. The monomeric $^{125}$I-CNTF was stored at 4° C. and used up to one week after preparation. As a test of structural and conformational integrity, $^{125}$I-CNTF (approximately 10,000 cpm) was mixed with a 5 µg unlabelled CNTF and analyzed by native gel electrophoresis. One major band was visible by either Coomassie staining or autoradiography. $^{125}$I-CNTF also showed comparable activity to native CNTF in supporting survival of E8 chick ciliary neurons in culture.

Tissue Culture Techniques

Superior cervical ganglia (SCG) from neonatal rats were treated with trypsin (0.1%), mechanically dissociated and plated on a polyornithine (30 µg/ml) substratum. Growth medium consisted of Ham's nutrient mixture F12 with 10% heat-inactivated fetal bovine serum (Hyclone), nerve growth factor (NGF) (100 ng/ml), penicillin (50 U/ml) and streptomycin (50 µg/ml). Cultures were maintained at 37° C. in a humidified 95% air/5% $CO_2$ atmosphere. Ganglion non-neuronal cells were eliminated by treatment with araC (10 µM) on days 1 and 3 of culture. Cultures were fed 3 times/week and were routinely used for binding assays within 2 weeks.

MG87/CNTFR is a fibroblast cell line transfected with the human CNTFα receptor gene (Squinto, et al.,1990, Neuron 5:757–766; Davis et al., 1991, Science 253:59–63).

Binding Assays

Binding was performed directly on cell monolayers. Cells in culture wells were washed once with assay buffer consisting of phosphate buffered saline (PBS; pH 7.4), 0.1 mM bacitracin, 1 mM PMSF, 1 µg/ml leupeptin, and 1 mg/ml BSA. After incubation with $^{125}$I-CNTF for 2 hours at room temperature, cells were quickly washed twice with assay buffer, lysed with PBS containing 1% SDS and counted in a Packard Gamma Counter. Non-specific binding was determined in the presence of 1,000-fold excess of unlabeled CNTF. Specific binding towards MG87/CNTFR was 80–90%. Data were analyzed using the GRAPHPAD program (ISI, Philadelphia, Pa.).

Results

Figure 4A:
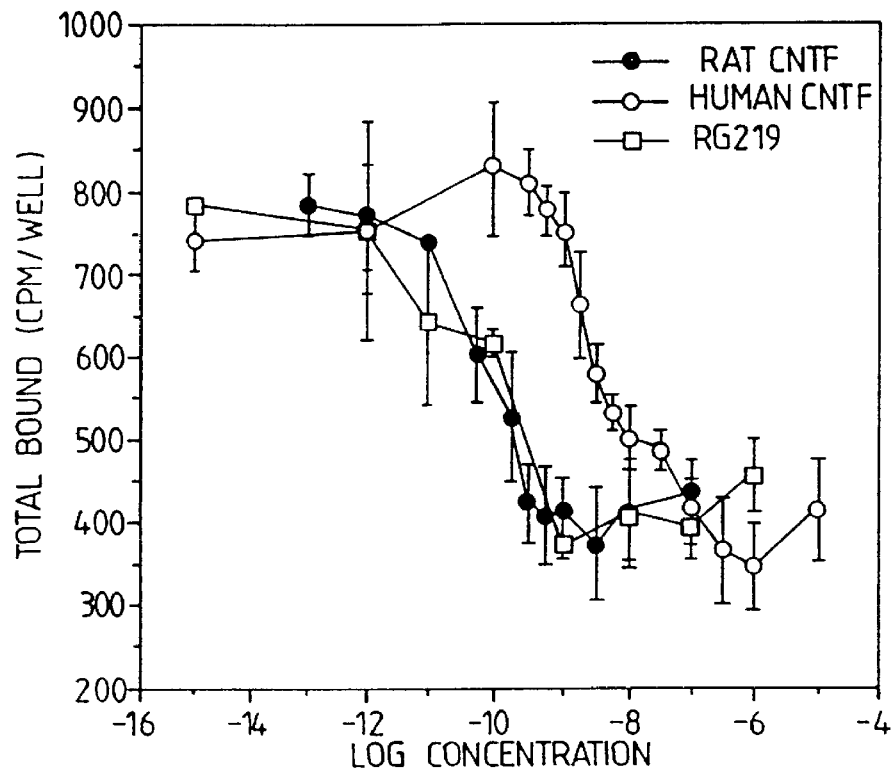
FIGS. 4A–4B Competitive ligand binding towards FIG. 4A.) SCG neurons and FIG. 4B.) MG87/huCNTFR fibroblasts. Standard deviation from the mean of three determinations is shown by vertical bars.

Competition curves of purified recombinant human, rat and CNTF RPN219 towards $^{125}$I-rat CNTF for binding on rat SCG neurons are shown in FIG. 4a. Both rat and human CNTF compete with $^{125}$I-rat CNTF for binding to SCG neurons, but human CNTF (IC50=25 nM) is 90 times less potent in displacing 125I-rat CNTF binding than unlabelled rat CNTF (IC50=0.28 nM). In contrast, RPN219 is almost as potent as rat CNTF and clearly more potent than human CNTF (IC50=0.3 nM).

Figure 4B:
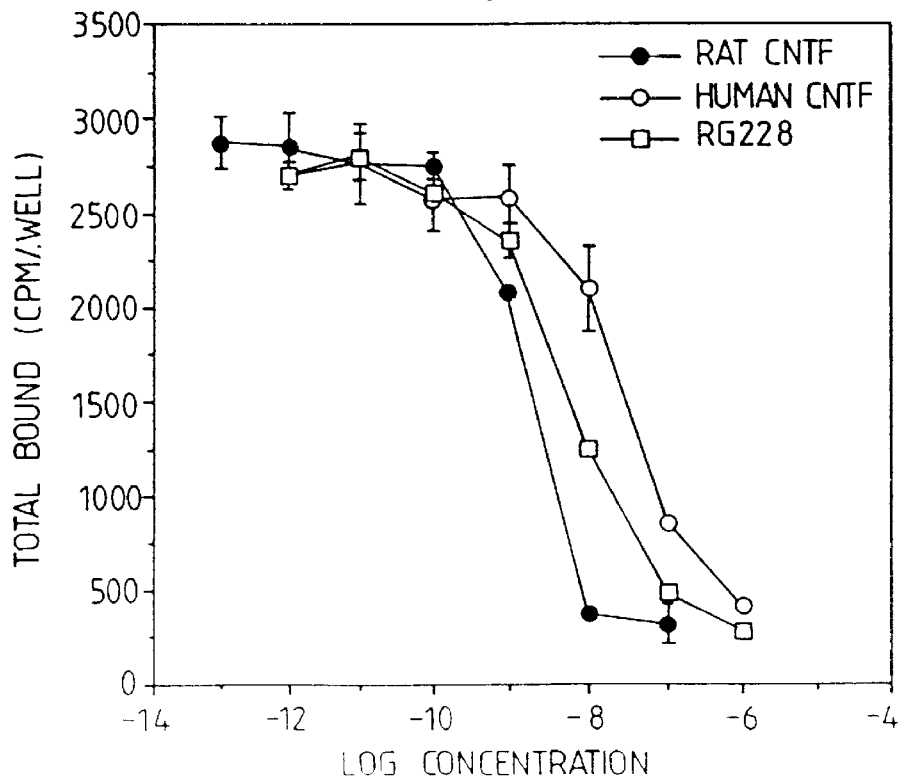

Similar results were obtained from competition experiments with mouse fibroblasts transfected with a plasmid directing the expression of the human CNTF receptor (FIG. 4b). Both rat, human and RPN228 compete with $^{125}$I-rat CNTF for binding to MG87/CNTFR cells. Human CNTF (IC50=30 nM) is 12 times less potent than rat CNTF (IC50=2.8 nM), whereas RPN228 is clearly more potent than the human protein (IC50=5.6 nM).

Competition binding experiments with the other modified CNTF proteins shown in FIGS. 1A & 1B also demonstrated that proteins having R63 displayed the biological activity of rat CNTF, whereas proteins having Q63 displayed the binding properties of human CNTF (data not shown). These results indicate that the single amino acid substitution (Q63→R) is sufficient to confer to human CNTF the receptor binding properties characteristic of rat CNTF.

Example 3

Measurement of Biological Activity of Modified CNTF Molecules

Materials and Methods

Recombinant CNTF was assayed on dissociated cultures of chick ciliary ganglion (CG) neurons as described (Masiakowski et al. 1991, id.), except that surviving cells were stained with MTT (Mosmann, T. 1983; J. Immunol. Methods 65:55–63).

Results

Figure 3A:
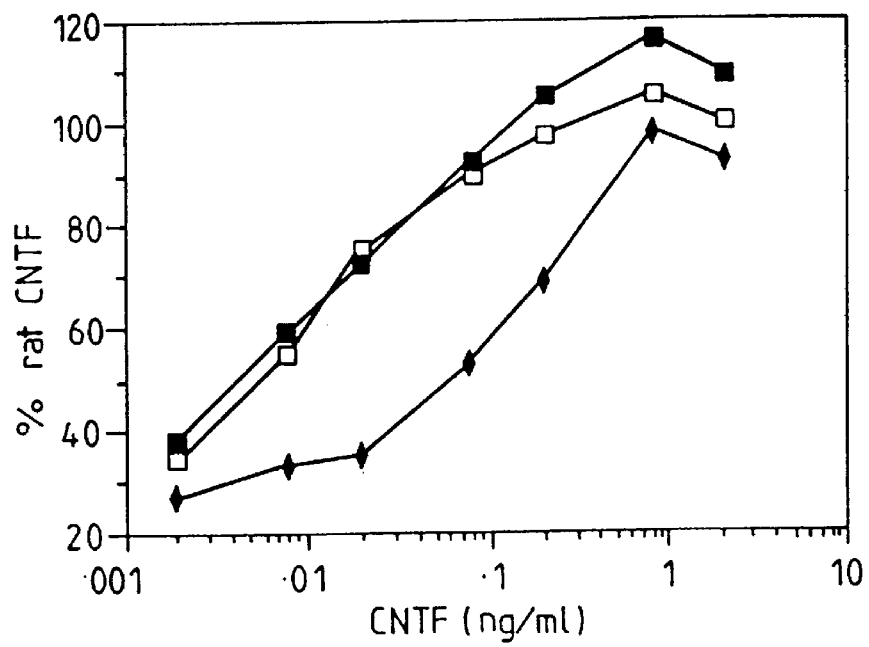
FIGS. 3A–3B Biological activity of two modified CNTF molecules FIG. 3A. human CNTF (filled diamonds), rat CNTF (open squares), and RPN219 (filled squares).
Figure 3B:
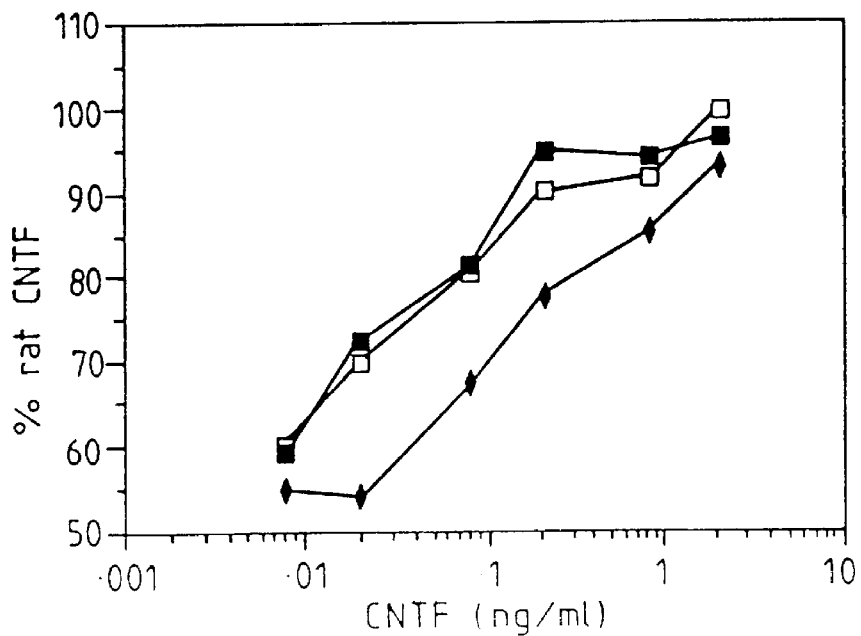

FIGS. 3A–3B shows dose-response curves of dissociated, neuron-enriched cultures of E8 chick embryo ciliary ganglia for purified recombinant human, rat and the modified CNTF proteins RPN219 and RPN228. By this assay, the biological activity of the chimeric proteins is indistinguishable from that of purified recombinant rat CNTF and clearly higher than that of recombinant human CNTF. Comparison of the dose-response curves in FIGS. 3A–3B also shows that the maximal levels of surviving neurons obtained with RPN219, RPN228 or rat CNTF are higher than those obtained with human CNTF. These results suggest that RPN219 and RPN228, like rat CNTF, are active towards a larger population of neurons than human CNTF. In parallel experiments, the biological activity of the other modified CNTF proteins shown in FIGS. 1A & 1B was examined. In every case, modified CNTF proteins carrying the (Q63→R) substitution displayed the biological activity of rat CNTF whereas proteins having Q63 displayed the activity of human CNTF (data not shown).

Overall, these results indicate that the single amino acid substitution (Q63→R) is sufficient to confer to human CNTF the biological activity of rat CNTF.

Example 4

Use of Modified CNTF To Prevent Light Induced Photoreceptor Injury

Albino rats of either the F344 or Sprague-Dawley strain were used at 2–5 months of age. The rats were maintained in a cyclic light environment (12 hr on: 12 hr off at an in-cage illuminance of less than 25 ft-c) for 9 or more days before being exposed to constant light. The rats were exposed to 1 or 2 weeks of constant light at an illuminance level of 115–200 ft-c (most rats received 125–170 ft-c) provided by two 40 watt General Electric "cool-white" fluorescent bulbs with a white reflector that was suspended 60cm above the floor of the cage. During light exposure, rats were maintained in transparent polycarbonate cages with stainless steel wire-bar covers.

Two days before constant light exposure, rats anesthetized with a ketamine-xylazine mixture were injected intravitreally with 1 μl of rat CNTF, human CNTF or modified CNTF [hCNTF (Q63→R)] dissolved in phosphate buffered saline (PBS) at a concentration of 0.1 to 500 ng/μl. The injections were made with the insertion of a 32 gauge needle through the sclera, choroid and retina approximately midway between the ora serrata and equator of the eye. In all cases, the injections were made into the superior hemisphere of the eye.

Immediately following constant light exposure, the rats were sacrificed by overdose of carbon dioxide followed immediately by vascular perfusion of mixed aldehydes. The eyes were embedded in epoxy resin for sectioning at 1 μm thickness to provide sections of the entire retina along the vertical meridian of the eye. The degree of light-induced retinal degeneration was quantified by assessing the degree of photoreceptor rescue by a 0–4+ pathologist's scale of rescue, 4+ being maximal rescue and almost normal retinal integrity. The degree of photoreceptor rescue in each section, as based on comparison to the control eye in the same rat, was scored by four individuals. This method has the advantage of considering not only the ONL thickness, but also more subtle degenerative changes to the photoreceptor inner and outer segments, as well as spatial degenerative gradients within the eye. Three eyes were examined for each time point to generate a dose response curve.

Results

The degree of rescue was measured for human, rat and hCNTF (Q63→R). The data indicated that both rat and hCNTF (Q63→R) had ten-fold greater ability to rescue photoreceptors in the light damage model than did recombinant human CNTF.

It is to be understood that while the invention has been described above in conjunction with preferred specific embodiments, the description and examples are intended to illustrate and not limit the scope of the invention, which is defined by the scope of the appended claims.

Example 5

Materials and Methods

Recombinant human CNTF variants were genetically engineered, expressed in *E. coli* and recovered at greater than 90% purity, as described previously (Masiakowski et al., 1991; Panayotatos et al., 1993).

The following stock solutions were prepared freshly in PBS at 5° C.:

rHCNTF . . . . . . . . . . . . . . . . . . . . . . . . . 0.5 mg/ml
RG160 (rHCNTF,ΔC13) . . . 0.5 mg/ml
RG162 (rHCNTF,17CA,ΔC13) . . . 0.5 mg/ml
RG290 (rHCNTF,63QR,ΔC13) . . . 1.2 mg/ml
RG297 (rHCNTF,17CA,63QR,ΔC13) . . . 0.4 mg/ml

To determine the stability of rHCNTF and several derivatives in physiological buffer at 37° C., stock solutions were dialyzed exhaustively against PBS at 5° C., diluted with PBS to 0.1 mg/ml and sterilized by filtration. Aliquots (0.2 ml), were transfered into 0.5 ml capacity polypropylene centrifugation tubes. The tubes were placed in a 37° C. incubator and, at the indicated times, individual tubes were removed and centrifuged at 15,000 rpm for 3 min at room temperature to separate soluble protein from insoluble precipitates. Supernatants were pipetted off into clean tubes containing an equal volume of 2× protein gel sample buffer, placed in a 85° C. bath for 2 min, mixed and stored at −20° C. until analysis by 15% SDS-PAGE. Pellets were resuspended in 1/10 original volume of water, mixed with an equal volume of 2× protein gel sample buffer and treated as above.

Methods for biological activity assays on E8 chick ciliary neurons and for protein gel electrophoresis have been described (Masiakowski et al., 1991; Panayotatos et al., 1993). Protein gel sample buffer (2×) consists of 12.5 ml TrisHCI, pH 6.8–20 ml glycerol–40 ml 10% SDS and 5 mg Bromophenol Blue per 100 ml.

Results

The solubility of rHCNTF is particularly limited in physiological buffer at neutral pH. Furthermore, the solubility over a broad pH range (4.5–8.0) depends strongly on the temperature and on the time of incubation. At 5° C., the solubility of rHCNTF in PBS is 1.4 mg/ml and the protein remains in solution for a few hours. In sharp contrast to the limited solubility of rHCNTF, the variant rHCNTF,ΔC13 can be concentrated to at least 12 mg/ml at 5° C. Despite this greater solubility, however, rHCNTF,ΔC13 still shows strong instability in physiological buffer, pH and temperature conditions. Upon incubation at 37° C., rHCNTF,ΔC13 falls out of solution at a rate that depends on the initial concentration.

Figure 5A:
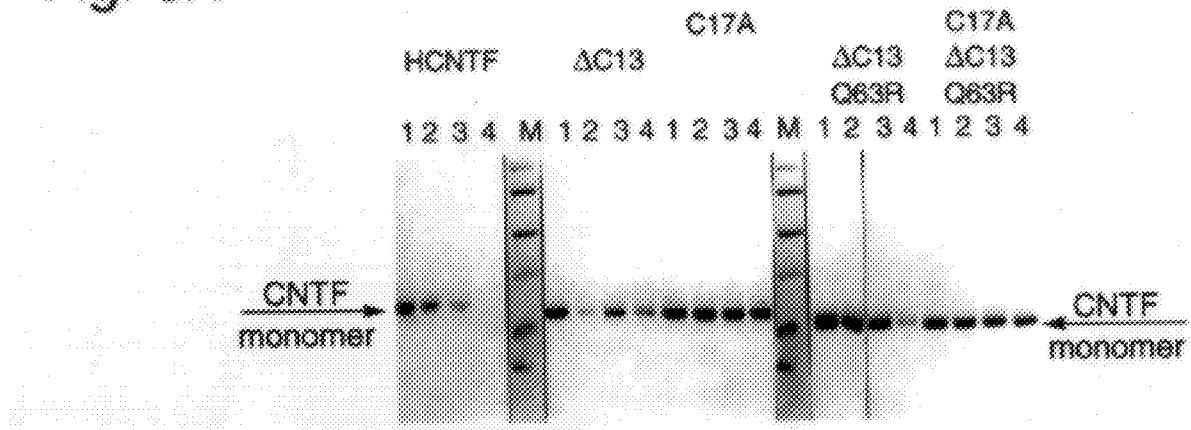
FIGS. 5A–5B Mobility of human and several modified CNTF molecules on SDS-15% polyacrylamide gels. Supernatant (FIG. 5A) and pellet (FIG. 5B—concentrated five fold) preparations of recombinant human CNTF (designated HCNTF) and several modified CNTF proteins were loaded as indicated. The modified proteins shown are ΔC13 (also known as RG160); 17CA,ΔC13 (RG162); ΔC13,63QR (RG290); and 17CA,ΔC13,63QR (RG 297). Markers of the indicated MW were loaded on lane M. Incubation in physiological buffer at 37° C. for 0, 2, 7 and 14 days is indicated in lanes 1–4, respectively.
Figure 5B:
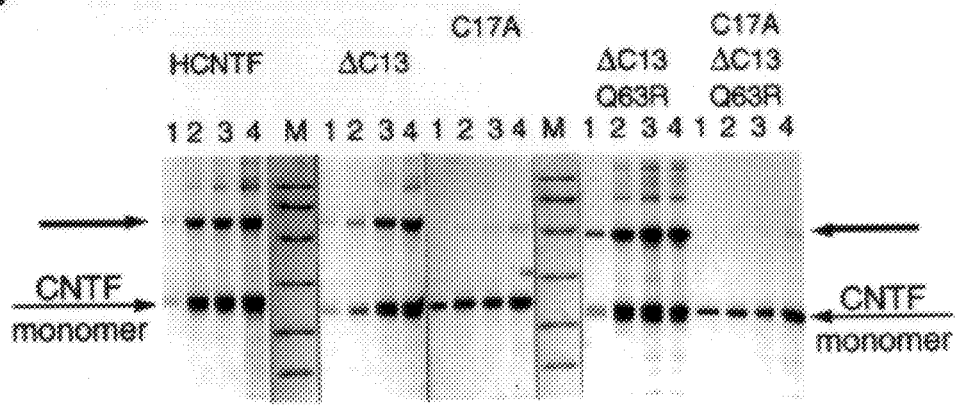

To determine the cause of this instability, we analyzed the physical integrity of rHCNTF and several variants in parallel experiments. FIGS. 5A & 5B shows that incubation of rHCNTF in physiological buffer at 37° C. for 0, 2, 7 and 14 days (lanes 1–4, respectively) caused progressive disappearance of the protein from the supernatants, accompanied by concomitant progressive appearance in the pellets. Furthermore, a good proportion of rHCNTF in the pellets appeared as a 48kD species that corresponded to the size of dimeric rHCNTF (FIG. 5B, double arrow). At longer incubation times, a small proportion of higher order aggregates was also evident. However, when the same samples were analyzed on the same type of gel but in the presence of disulfide reducing agents, the 48 kD species was converted to monomeric rHCNTF, evidence that the 48 kD species represents rHCNTF dimers covalently linked by disulfide bonds. Such dimers would be expected to form through the unique cysteine residue of rHCNTF. Therefore, these results indicated that the instability of rHCNTF at 37° C. is caused by aggregation initiated by intermolecular disulfide bond formation.

Similar results were obtained with two rHCNTF variants, rHCNTF,ΔC13 and rHCNTF,63QR,ΔC13, except that the appearance of insoluble aggregates in the pellets was somehow slower in the case of rHCNTF,ΔC13 (FIG. 5B). Given the fact that the ΔC13 deletion confers to rHCNTF much greater solubility in physiological buffer, the improved stability of rHCNTF,ΔC13 is most likely an indirect consequence of its greater solubility.

To further test the possibility that the instability of rHCNTF at 37° C. is caused by aggregation initiated by intermolecular disulfide bond formation, the unique cysteine residue at position 17 was substituted by alanine, using established genetic engineering methodology. The two rHCNTF variants, rHCNTF,17CA,ΔC13 and rHCNTF,17CA,63QR,ΔC13 generated by this process were subjected to the same analysis by non-reducing 15% SDS-PAGE. FIGS. 5A–5B shows that even after incubation for 14 days at 37° C. both proteins remained soluble with no evidence of dimerization or aggregate formation. Even in the small proportion of protein found in the pellets, which represented mostly the small amount of soluble protein remaining in the centrifuge tubes after removal of the supernatant, there was little evidence of dimerization. These results confirmed the conclusion that the instability of rHCNTF is caused by aggregation initiated by intermolecular disulfide bond formation, and demonstrated that elimination of the free -SH functional group in other rHCNTF variants, e.g. RG297, also result in greater stability.

Figure 6:
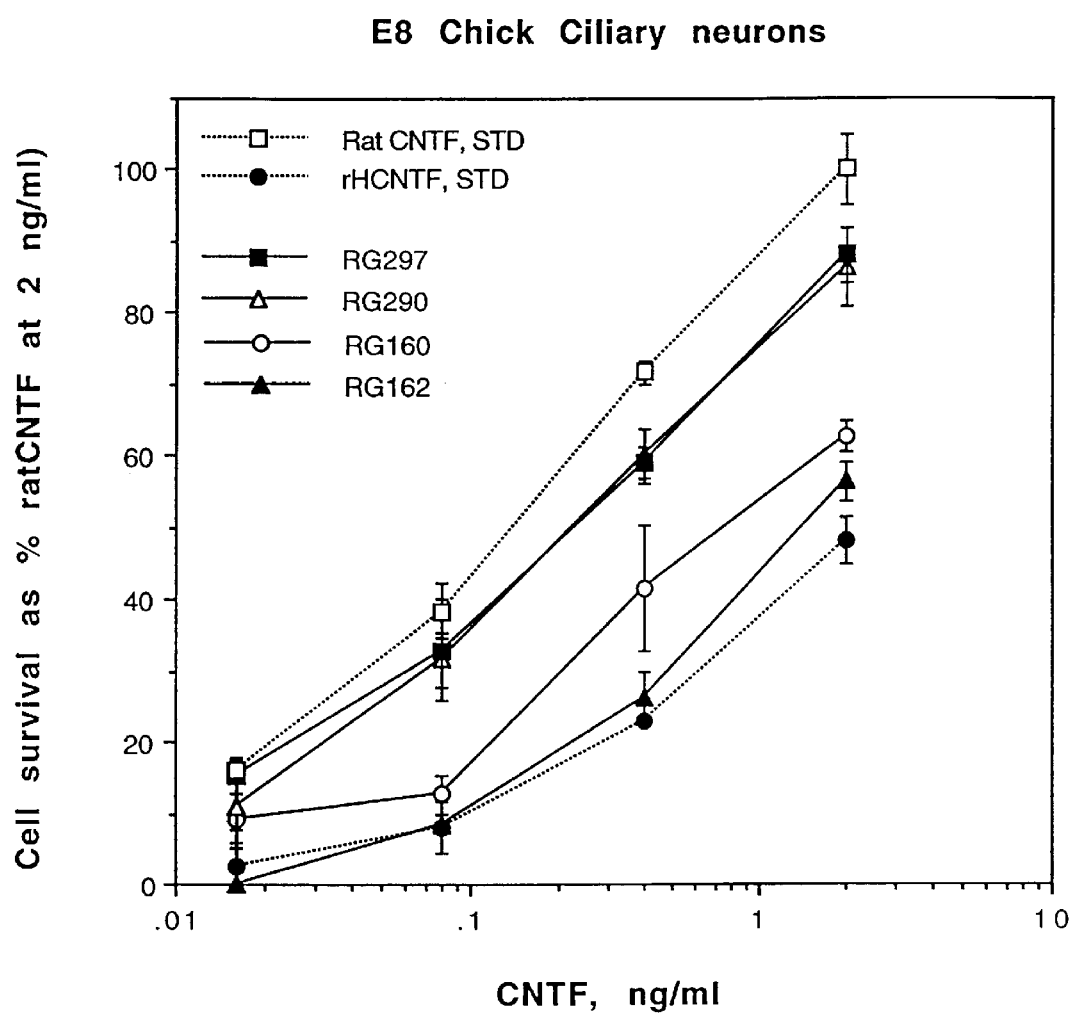
FIG. 6—Survival of primary dissociated E8 chick ciliary neurons in response to increasing concentrations of various CNTF variants. Control concentration response curves for rat CNTF and rHCNTF obtained with standard, untreated stock solutions, as well as with four rHCNTF variants, RG297, RG290, RG160 and RG162.
Figure 7:
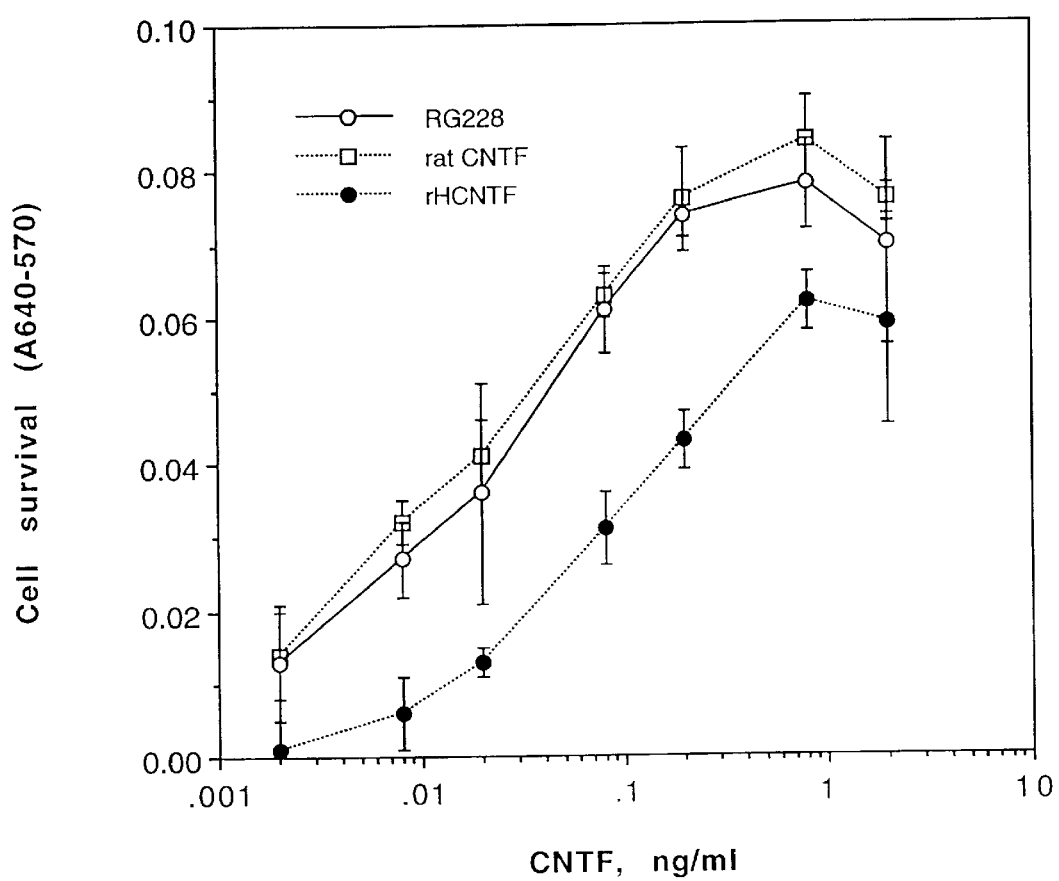
FIG. 7—Survival of primary dissociated E8 chick ciliary neurons in response to increasing concentrations of various CNTF variants. Control concentration response curves for rat CNTF and rHCNTF obtained with standard, untreated stock solutions, as well as with rHCNTF variant RG228 (also known as RPN228 and having the mutation 63QR).

To test whether the proteins remaining in solution after incubation at 37° C. were still biologically active, samples were analyzed for neuronal survival activity. FIG. 6 shows control concentration response curves for rat CNTF and rHCNTF obtained with standard, untreated stock solutions, as well as with four rHCNTF variants incubated for 7 days at 37° C. Of the latter, the proteins carrying the 17CA mutation, RG297 and RG162, were assayed at their nominal concentrations, whereas RG290 and RG160 were assayed after correcting their concentrations for the amount of protein remaining in solution. FIG. 6 shows that the concentration response curves displayed by these compounds are those expected from these proteins in their fully active form: RG160 and RG162 show the same potency as rHCNTF within experimental error, whereas RG290 and RG297 that carry the 63QR substitution show 4–5 fold higher potency than rHCNTF, as previously observed (Panayotatos, N., et al., (1993)) and as shown in FIG. 7. Therefore, incubation of rHCNTF and its derivatives at 37° C. for 7 days does not cause loss of biological activity, only loss of protein through dimerization followed by precipitation.

Example 6

Materials and Methods

Protein Engineering and Purification—The following rHCNTF variants were compared to rHCNTF:

RG228 (rHCNTF,63QR);

RG297 (rHCNTF,17CA,63QR,ΔC13)

RG242 (rHCNTF,63QR64WA)

These proteins were genetically engineered, expressed in *E. coli* and recovered at greater than 90% purity by the methodology described for rHCNTF (Masiakowski et al., 1991; Panayotatos et al., 1993).

Biological Activity Assays—Methods for biological activity assays on E8 chick ciliary neurons have been described (Panayotatos et al., 1993).

Pharmacokinetic Determinations—Rats were injected intravenously (i.v.) with rHCNTF (n=1) and RG242 (n=2) at 100 μg/kg and with RG228 (n=1) at 200 μg/kg. Rats were also injected subcutaneously (s.c.) with rHCNTF (n=2), RG242 (n=2) and RG228 (n=1) at 200 μg/kg. Blood specimens were collected prior to dosing and at various times after dosing and were processed to obtain plasma. The plasma specimens were analyzed using the rHCNTF ELISA method for rodent plasma (D.B. Lakings, et al. DSER 93/DMAP/006, "Dose Proportionality and Absolute Bioavailability of rHCNTF in the Rat Following Subcutaneous Administration at Eight Dose Levels" (Phoenix International Project No. 920847) 10 Nov. 1993). The plasma concentrations were evaluated using non compartment techniques. A standard curve for each compound was included on each assay plate and was used to calculate the amount of that compound present in the specimens analyzed on the plate. The sensitivity of the assay varied among compounds by less than twofold.

Efficacy and Toxicity Determinations In Vivo—Male Sprague-Dawley rats weighing ~220 g were anesthetized before surgery. The right sciatic nerve was transected at the level of the knee and a 5 mm segment of nerve was removed. Sham surgeries were performed on the left side of each animal. Starting the morning after surgery, rats were weighed and administered vehicle (either PBS or lactate/phosphate/mannitol, pH 4.5) or the rHCNTF compound to be tested, dissolved in the same vehicle at doses ranging from 0.01–1.0 mg/kg, s.c. Rats were weighed and injected daily for 1 week, at which time they were sacrificed and the soleus muscles dissected and weighed. The ratio of the right (denervated) to left (sham) soleus wet weights for each animal was calculated to assess the degree of atrophy caused by denervation and the prevention thereof by treatment with each compound. For assessment of toxicity, the body weights were calculated as a percent of the weight gain of vehicle-treated rats. Both vehicle solutions produced similar results in atrophy and body weight gain.

Results

Figure 8:
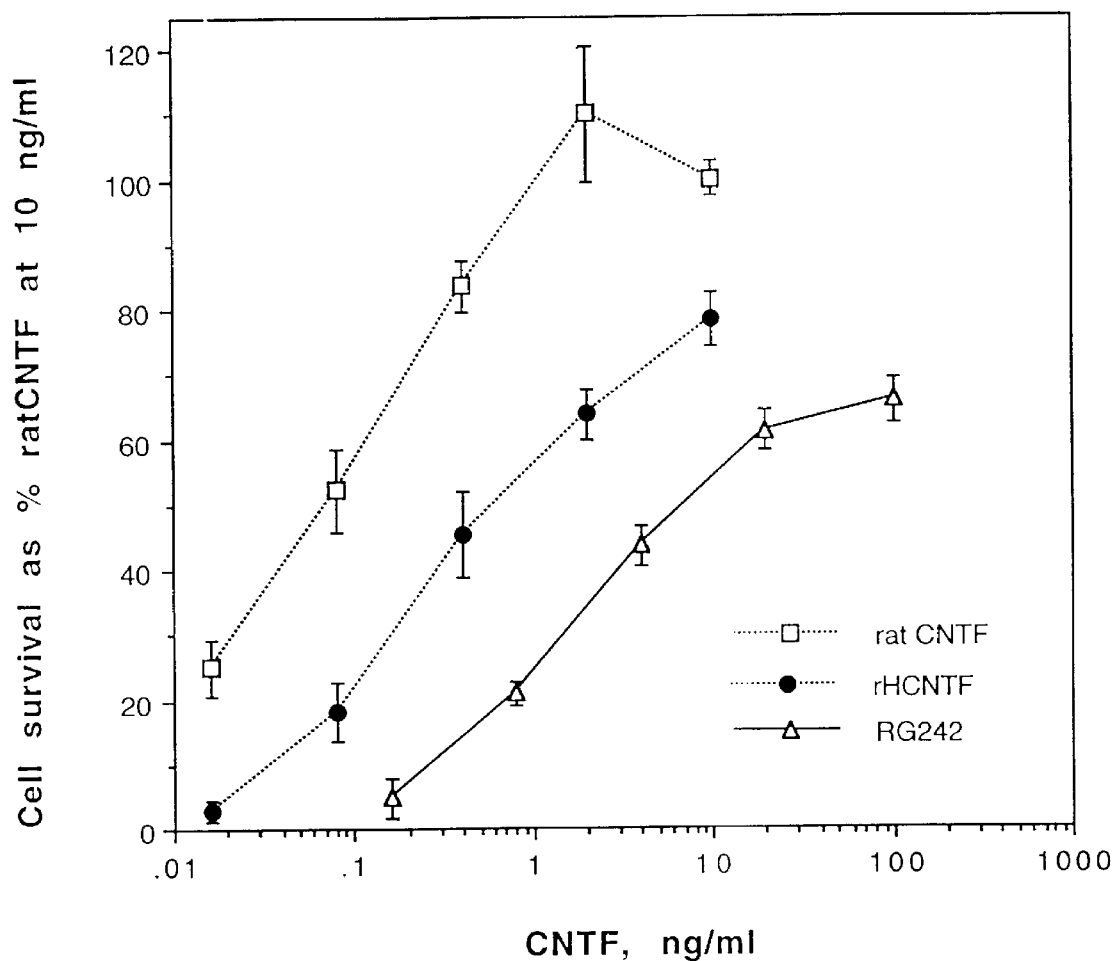
FIG. 8—Survival of primary dissociated E8 chick ciliary neurons in response to increasing concentrations of various CNTF variants. Control concentration response curves for rat CNTF and rHCNTF obtained with standard, untreated stock solutions, as well as with rHCNTF variant RG242 (which has the mutation 63QR,64WA).

Biological Activity In vitro—To characterize the activity of rHCNTF in vitro, we measured its effect on mediating the survival of primary dissociated E8 chick ciliary neurons. Neuronal survival in response to increasing concentrations of various human CNTF variants is shown in FIGS. 6, 7 and 8. The variants RG228 (FIG. 7) and RG297 (FIG. 8) that carry the 63QR substitution show 4–5 times greater potency than rHCNTF but the variant RG242 showed a 10-fold weaker potency than rHCNTF, despite the fact that it carries the 63QR substitution. Thus, introduction of various amino acid side chains at various positions of the CNTF sequence has very different effects on the survival of primary neurons in vitro that vary from great loss to strong gain of activity relative to rHCNTF.

Pharmacokinetics—Before attempting to correlate the in vitro biological potency of a set of compounds to their pharmacological efficacy in vivo, it is useful to determine their absolute bioavailability in the same animal model. In the experiments described below, the disposition kinetics after i.v. administration and the absolute bioavailability after s.c. administration of RG228 and RG242 were determined and compared to those of rHCNTF.

Figure 9:
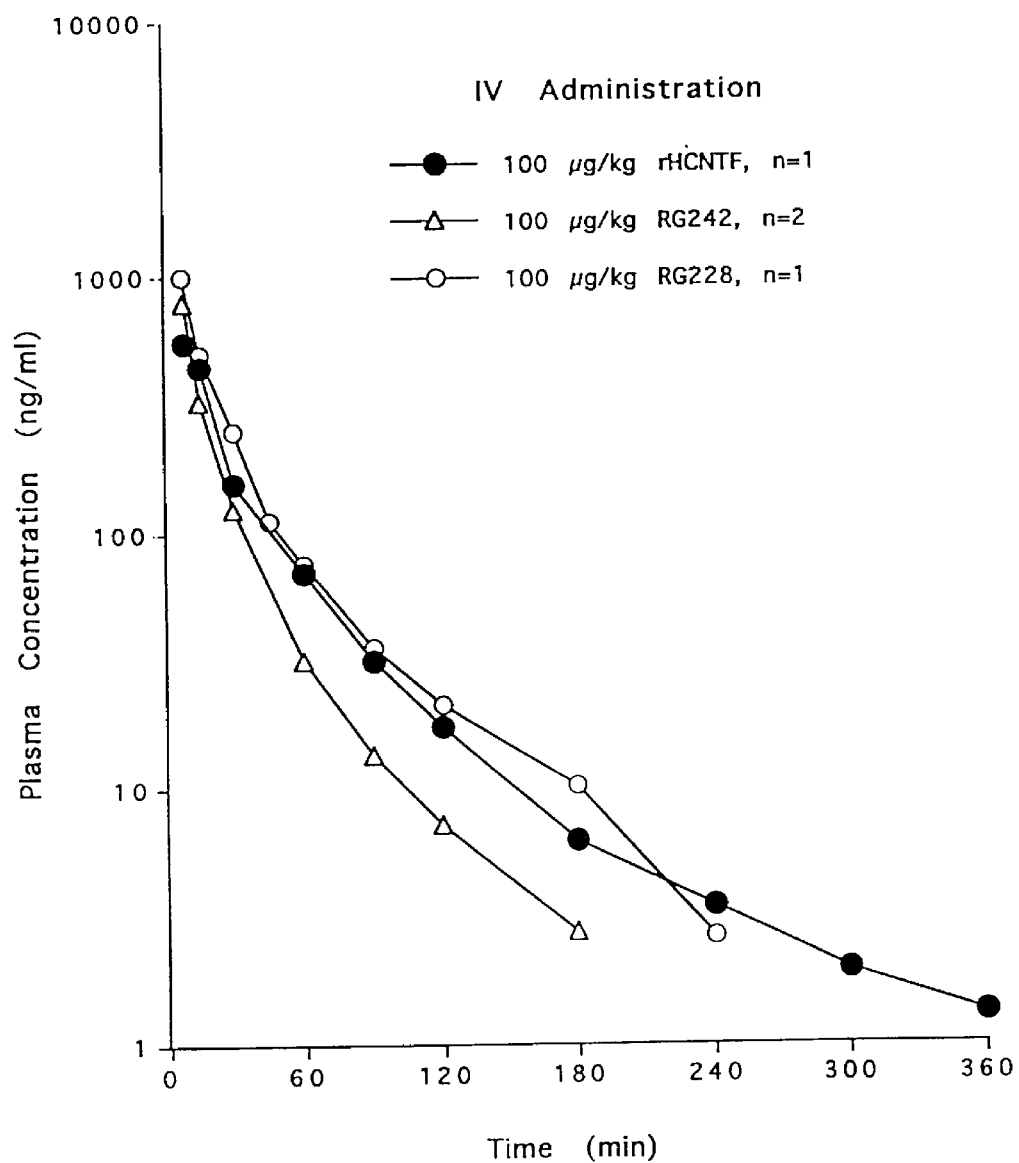
FIG. 9—Average plasma concentration time profiles in the rat after intravenous (IV) administration of rHCNTF, RG228 and RG242 normalized to 100 μg/kg dose for all three compounds.

The average plasma concentration time profiles in the rat after IV administration of rHCNTF, RG228 and RG242 are shown in FIG. 9, normalized to 100 μg/kg dose for all three compounds. The average pharmacokinetic parameters are summarized in Table 1.

After i.v. administration to rats, RG242 had a distribution phase α somewhat faster than that of rHCNTF and RG228. The disposition phase β for RG242 and RG228 was faster than that of rHCNTF. Thus, RG242 appeared to be distributed into the body and cleared from systemic circulation somewhat more rapidly than rHCNTF, whereas RG228 appeared to be distributed into the body as fast as rHCNTF and cleared from systemic circulation somewhat faster. The area under the concentration time curve (AUC) for RG242 was comparable to that of rHCNTF, indicating that the total body clearance ($Cl_T$) was about the same for the two compounds. A twice larger area was observed with RG228. However, the apparent volume of distribution ($V_{area}$), which is a function of both β and AUC, was approximately twofold smaller for both RG228 and RG242 relative to rHCNTF, suggesting that these variants are distributed less widely. The limited number of animals used in these evaluations did not allow the quantitative distinction of these values. However, these results clearly indicate that the distribution and disposition kinetics of RG228 and RG242 after i.v. administration are not substantially different from those of rHCNTF.

Figure 10:
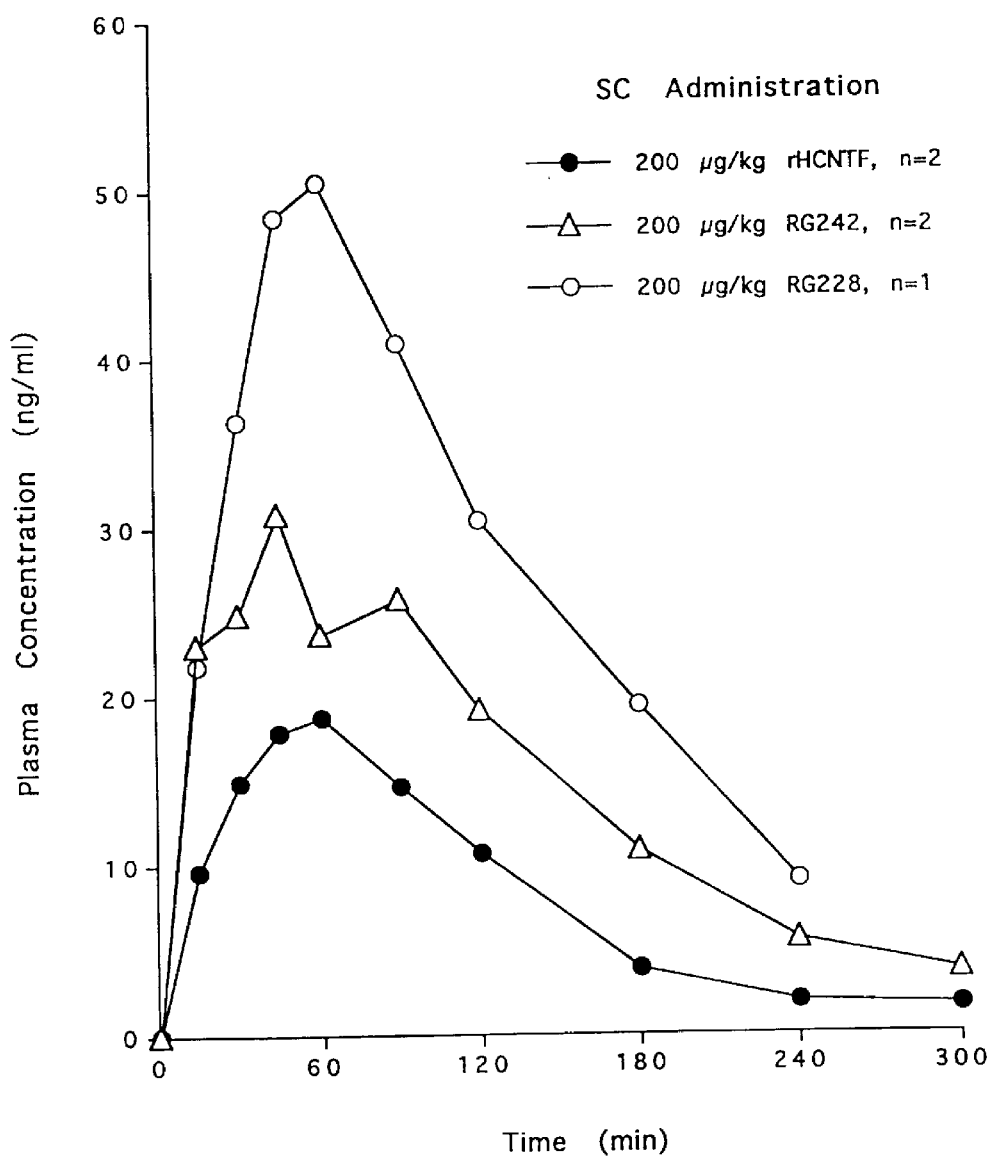
FIG. 10—Average plasma concentration time profiles in the rat after subcutaneous (SC) administration of rHCNTF, RG228 and RG242 normalized to 200 μg/kg dose for all three compounds.

After s.c. administration, RG228 and RG242 had a 2–3 fold longer absorption phase (Ka) relative to rHCNTF (FIG. 10 and Table 2). The disposition phase of RG242 was also somewhat longer. The longer apparent terminal disposition phase of RG242 after s.c. dosing compared to i.v. administration may be attributed to the incomplete characterization of the terminal phase after the i.v. injection. Overall, the absolute bioavailability of RG228 (13.7%) and RG242 (10.9%) were comparable to that of rHCNTF (6.0%), in view of the fact that in two previous independent studies, the absolute bioavailability of rHCNTF was found to be 14.2% (n=18) and 7.5% (n=8) (D. B. Lakings, et al., DSER 93/DMAP/006, "Dose Proportionality and Absolute Bioavailability of rHCNTF in the Rat Following Subcutaneous Administration at Eight Dose Levels" (Phoenix International Project No. 920847) 10 Nov. 1993; D. B. Lakings, et al., Dose Proportionality and Absolute Bioavailability of rHCNTF Administered Subcutaneously to Rats. AAPS Ninth Annual Meeting, San Diego, Calif., November, 1994). Therefore, the bioavailabilities of rHCNTF, RG228 and RG242 are not significantly different within experimental error.

Figure 11A:
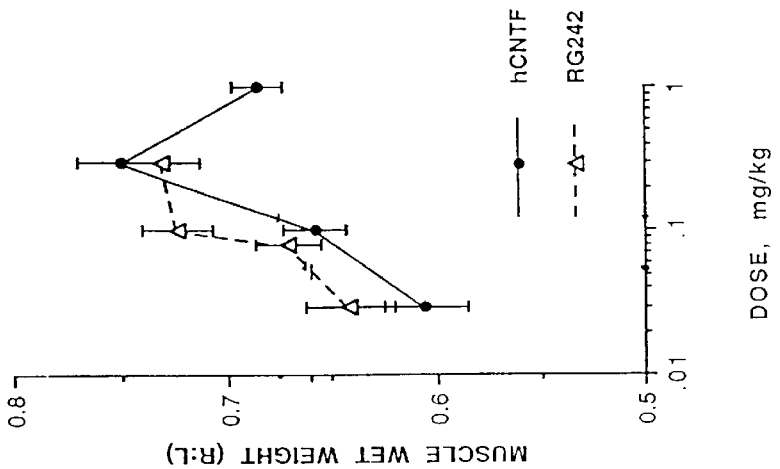
FIG. 11A to 11C —Comparison of dose dependent rescue of rat muscle wet weight of (FIG. 11A) hCNTF vs. RG228.
Figure 11B:
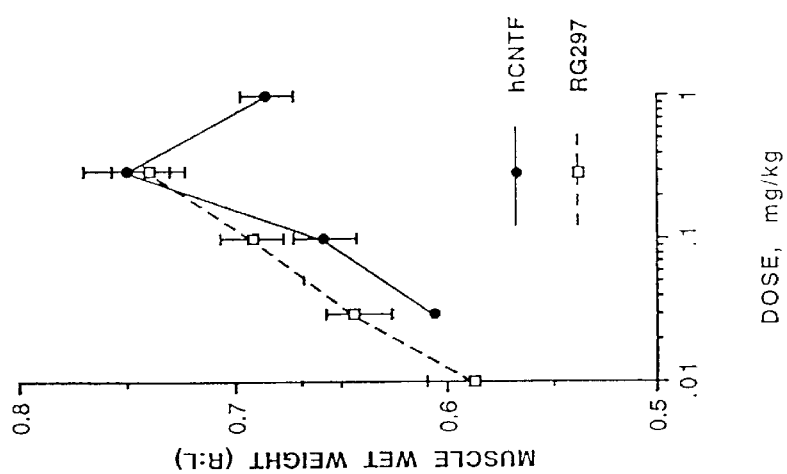
Figure 11C:
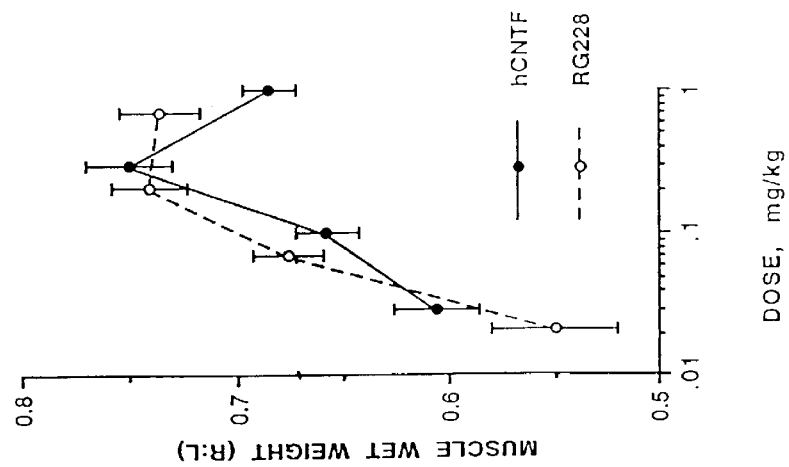
Figure 12:
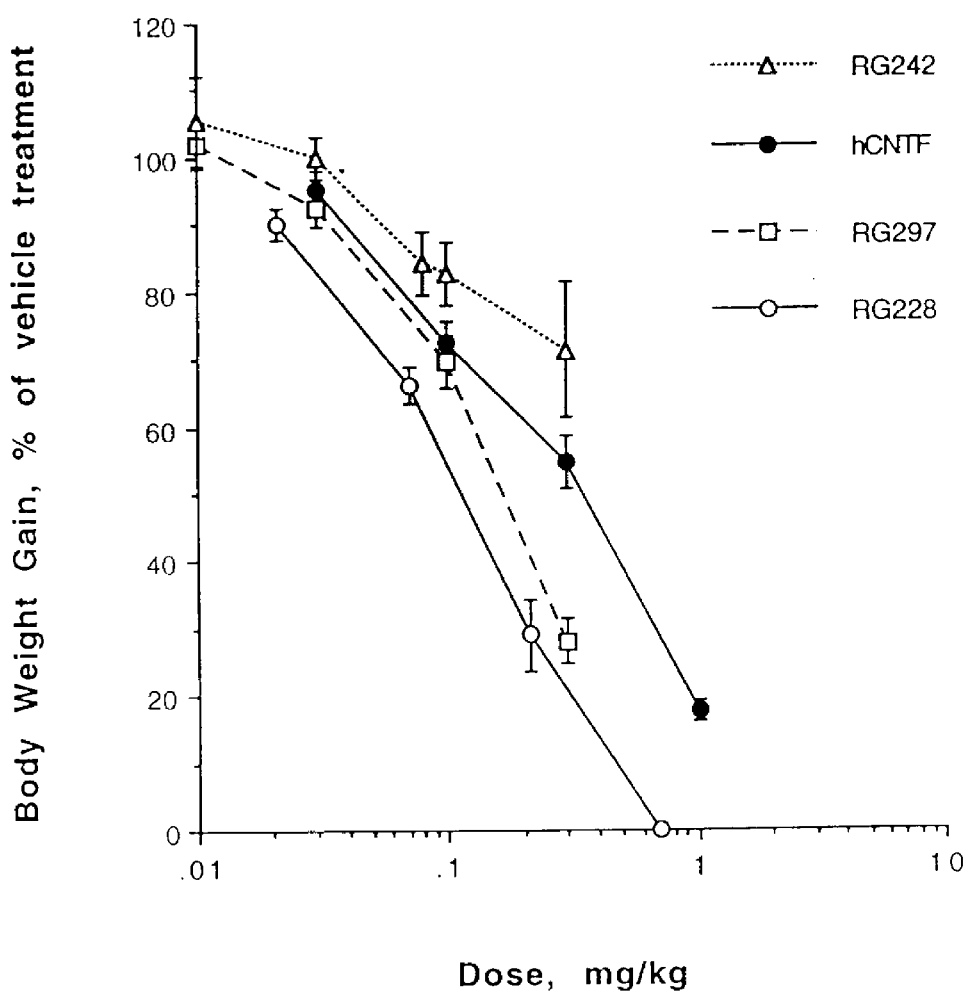
FIG. 12—Comparison of in vivo toxicity for hCNTF, RG228, RG242 and RG297.

Efficacy and Toxicity In vivo—In control experiments, denervation of the soleus muscle resulted in a loss of 40% of muscle wet weight by 7 days. This value is very accurate and reproducible, since it varies by only 3% among independent experiments. Daily administration of rHCNTF resulted in a dose-dependent rescue of muscle wet weight at an $ED_{50}$=0.12 mg/kg and a maximal effect at 0.3 mg/kg (FIGS. 11A–11C). At the same time, even though animals continued to gain weight during the course of these experiments, they clearly did not gain as much as their vehicle-treated counterparts (p<0.01; FIG. 12), especially at the maximally efficacious doses.

In the course of several experiments conducted in parallel with rHCNTF, it was determined that the 63QR substitution resulted in a 2-fold increase in potency in vivo (FIG. 11A–11C) but, also, a concomitant 2 fold increase in toxicity (FIG. 12). In contrast, RG297, which carries the additional C17A and ΔC13 modifications, shows a 2.6 fold greater potency but the same toxicity relative to rHCNTF. Finally, RG242 produced a 2.8 fold increased potency and an 2.4 fold decreased toxicity relative to rHCNTF. These results are summarized in Table 3.

The relative therapeutic index (T.I.) for each of these compounds was calculated as the ratio of the $TD_{25}$ and $ED_{50}$ values, normalized to that of rHCNTF. While the T.I. of RG228 is equal to that of rHCNTF, the T.I. of RG297 and RG242 is 2.5 and 6.8 fold superior to that of rHCNTF, respectively.

Therefore, RG297 and RG242 have superior pharmacological properties than rHCNTF. This is of great relevance to the clinical situation where decreased body weight is observed upon rHCNTF treatment in humans.

One skilled in the art will recognize that other alterations in the amino acid sequence of CNTF can result in a biologically active molecule which may have enhanced properties. For example, applicant has prepared a 17CS mutant which has a serine residue in place of the cysteine residue at position 17 and is biologically active. Applicant has also prepared a biologically active quadruple mutant, 17CA,ΔC13,63QR,64WA. Further CNTF mutants, all of which retain biological activity, are set forth in Table 4.

TABLE 1

Average Pharmacokinetic Parameters for rHCNTF, RG228 and RG242 after Intravenous Administration to Rats at 100 µg/kg.

| Pharmacokinetic Parameter | Compound | | |
|---|---|---|---|
| | rHCNTF | RG242 | RG228* |
| n | 1 | 2 | 1 |
| $C_0$ (ng/ml) | 726 | 2,175 | NC |
| $AUC_{0-\infty}$ (ng.min/ml) | 20,230 | 22,890 | 55,800 |
| $\alpha$ (min$^{-1}$) | 0.0492 | 0.0856 | 0.041 |
| $t_{1/2\alpha}$ (min) | 14 | 8 | 17 |
| $\beta$ (min$^{-1}$) | 0.0106 | 0.0200 | 0.0176 |
| $t_{1/2\beta}$ (min) | 65 | 35 | 39 |
| $V_{area}$ (ml/kg) | 470 | 220 | 204 |
| $Cl_T$ (ml/min/kg) | 4.9 | 4.4 | 3.6 |

*RG228 values normalized to a 100 µg/kg i.v. dose to be comparable to the other two compounds that were administered at 100 µg/kg.
$C_0$: Estimated by extrapolation of the first two plasma concentrations to time zero.
NC: Not calculated

TABLE 2

Average Pharmacokinetic Parameters for rHCNTF, RG228 and RG242 After Subcutaneous Administration to Rats at 200 µg/kg

| Pharmacokinetic Parameter | Compound | | |
|---|---|---|---|
| | rHCNTF | RG242 | RG228 |
| n | 2 | 2 | 1 |
| $C_{max}$ (ng/ml) | 18 | 32 | 50 |
| $T_{max}$ (min) | 30–45 | 30–45 | 60 |
| $AUC_{0-\infty}$ (ng.min/ml) | 2,425 | 4,980 | 7,620 |
| Absolute Bioavailability | 6.0 | 10.9 | 13.7 |
| $k_e$ (min$^{-1}$) | 0.0133 | 0.0083 | NC |
| $t_{1/2ke}$ (min) | 52 | 82 | NC |
| $k_a$ (min$^{-1}$) | 0.0401 | 0.0180 | 0.0102 |
| $t_{1/2ka}$ (min) | 17 | 39 | 68 |

NC: Not calculated.

TABLE 3

Efficacy, Toxicity and Therapeutic Index of rHCNTF and Derivatives

| Compound | $ED_{50}$ (mg/kg) | $TD_{25}$ (mg/kg) | Therapeutic Index ($TD_{25}/ED_{50}$) | Relative Therapeutic Index |
|---|---|---|---|---|
| rHCNTF | 0.12 | 0.087 | 0.72 | 1.0 |
| RG228 | 0.065 | 0.047 | 0.72 | 1.0 |
| RG297 | 0.045 | 0.080 | 1.78 | 2.5 |
| RG242 | 0.043 | 0.21 | 4.88 | 6.8 |

Table 4

Biological activity of rHCNTF variants on E8 chick ciliary neurons. Potency units (1/$EC_{50}$) are shown relative to human CNTF which is assigned a value of 100. One potency unit is defined as the reciprocal ligand concentration showing the same biological activity as 1 ng/ml rHCNTF.

| CNTF | POTENCY |
|---|---|
| rat | 500.0 |
| human | 100.0 |
| 17CS | 100.0 |
| 63QA | 87.0 |
| 63QN | 100.0 |
| 63QH | 2.5 |
| 63QE | <1 |
| 63QK | 1.1 |
| 63QR | 400.0 |
| 64WA | 2.0 |
| 63QR64WA | 9.0 |
| 63QR64WF | 250.0 |
| 63QR64WH | 25.0 |
| 63QR64WQ | 10.0 |

FIGS. 13A–13B—Sequence of Human CNTF. Human nucleic acid (SEQ ID No. 20) and amino acid (SEQ ID NO. 21) sequences.

---

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 200 amino acids
        ( B ) TYPE: amino acid
        ( C ) STRANDEDNESS: single
        ( D ) TOPOLOGY: unknown ( i i ) MOLECULE TYPE: protein ( x i ) SEQUENCE DESCRIPTION: SEQ ID NO:1:

```
Met  Ala  Phe  Thr  Glu  His  Ser  Pro  Leu  Thr  Pro  His  Arg  Arg  Asp  Leu
1                   5                   10                          15

Cys  Ser  Arg  Ser  Ile  Trp  Leu  Ala  Arg  Lys  Ile  Arg  Ser  Asp  Leu  Thr
            20                  25                          30

Ala  Leu  Thr  Glu  Ser  Tyr  Val  Lys  His  Gln  Gly  Leu  Asn  Lys  Asn  Ile
         35                  40                          45
```

```
Asn  Leu  Asp  Ser  Ala  Asp  Gly  Met  Pro  Val  Ala  Ser  Thr  Asp  Gln  Trp
     50                       55                      60

Ser  Glu  Leu  Thr  Glu  Ala  Glu  Arg  Leu  Gln  Glu  Asn  Leu  Gln  Ala  Tyr
65                       70                      75                           80

Arg  Thr  Phe  His  Val  Leu  Leu  Ala  Arg  Leu  Leu  Glu  Asp  Gln  Gln  Val
               85                       90                      95

His  Phe  Thr  Pro  Thr  Glu  Gly  Asp  Phe  His  Gln  Ala  Ile  His  Thr  Leu
                100                      105                     110

Leu  Leu  Gln  Val  Ala  Ala  Phe  Ala  Tyr  Gln  Ile  Glu  Glu  Leu  Met  Ile
          115                      120                     125

Leu  Leu  Glu  Tyr  Lys  Ile  Pro  Arg  Asn  Glu  Ala  Asp  Gly  Met  Pro  Ile
     130                      135                     140

Asn  Val  Gly  Asp  Gly  Gly  Leu  Phe  Glu  Lys  Lys  Leu  Trp  Gly  Leu  Lys
145                      150                     155                          160

Val  Leu  Gln  Glu  Leu  Ser  Gln  Trp  Thr  Val  Arg  Ser  Ile  His  Asp  Leu
                165                      170                     175

Arg  Phe  Ile  Ser  Ser  His  Gln  Thr  Gly  Ile  Pro  Ala  Arg  Gly  Ser  His
               180                      185                     190

Tyr  Ile  Ala  Asn  Asn  Lys  Lys  Met
          195                     200
```

(2) INFORMATION FOR SEQ ID NO:2:

(i) SEQUENCE CHARACTERISTICS:
        (A) LENGTH: 200 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO:2:

```
Met  Ala  Phe  Ala  Glu  Gln  Thr  Pro  Leu  Thr  Leu  His  Arg  Arg  Asp  Leu
1                   5                        10                     15

Cys  Ser  Arg  Ser  Ile  Trp  Leu  Ala  Arg  Lys  Ile  Arg  Ser  Asp  Leu  Thr
               20                      25                      30

Ala  Leu  Met  Glu  Ser  Tyr  Val  Lys  His  Gln  Gly  Leu  Asn  Lys  Asn  Ile
          35                       40                      45

Asn  Leu  Asp  Ser  Val  Asp  Gly  Val  Pro  Val  Ala  Ser  Thr  Asp  Arg  Trp
     50                       55                      60

Ser  Glu  Met  Thr  Glu  Ala  Glu  Arg  Leu  Gln  Glu  Asn  Leu  Gln  Ala  Tyr
65                       70                      75                           80

Arg  Thr  Phe  Gln  Gly  Met  Leu  Thr  Lys  Leu  Leu  Glu  Asp  Gln  Arg  Val
               85                       90                      95

His  Phe  Thr  Pro  Thr  Glu  Gly  Asp  Phe  His  Gln  Ala  Ile  His  Thr  Leu
                100                      105                     110

Met  Leu  Gln  Val  Asp  Ala  Phe  Ala  Tyr  Gln  Leu  Glu  Glu  Leu  Met  Val
          115                      120                     125

Leu  Leu  Glu  Gln  Lys  Ile  Pro  Glu  Asn  Glu  Ala  Asp  Gly  Met  Pro  Ala
     130                      135                     140

Thr  Val  Gly  Asp  Gly  Gly  Leu  Phe  Glu  Lys  Lys  Leu  Trp  Gly  Leu  Lys
145                      150                     155                          160

Val  Leu  Gln  Glu  Leu  Ser  Gln  Trp  Thr  Val  Arg  Ser  Ile  His  Asp  Leu
                165                      170                     175

Arg  Val  Ile  Ser  Ser  His  Gln  Met  Gly  Ile  Ser  Ala  Leu  Glu  Ser  His
               180                      185                     190
```

```
        Tyr  Gly  Ala  Lys  Asp  Lys  Gln  Met
                  195                      200
```

(2) INFORMATION FOR SEQ ID NO:3:

(i) SEQUENCE CHARACTERISTICS:
        (A) LENGTH: 199 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO:3:

```
Met  Ala  Phe  Met  Glu  His  Ser  Ala  Leu  Thr  Pro  His  Arg  Arg  Glu  Leu
1                   5                        10                       15

Cys  Ser  Arg  Thr  Ile  Trp  Leu  Ala  Arg  Lys  Ile  Arg  Ser  Asp  Leu  Thr
               20                       25                  30

Ala  Leu  Thr  Glu  Ser  Tyr  Val  Lys  His  Gln  Gly  Leu  Asn  Lys  Asn  Ile
          35                       40                       45

Asn  Leu  Asp  Ser  Val  Asp  Gly  Val  Pro  Met  Ala  Ser  Thr  Asp  Gln  Trp
     50                       55                       60

Ser  Glu  Leu  Thr  Glu  Ala  Glu  Arg  Leu  Gln  Glu  Asn  Leu  Gln  Ala  Tyr
65                       70                       75                       80

Arg  Thr  Phe  His  Ile  Met  Leu  Ala  Arg  Leu  Leu  Glu  Asp  Gln  Gln  Val
               85                       90                       95

His  Phe  Thr  Pro  Ala  Glu  Gly  Asp  His  Phe  Gln  Ala  Ile  His  Thr  Leu
               100                      105                      110

Leu  Leu  Gln  Val  Ala  Ala  Phe  Ala  Tyr  Gln  Ile  Glu  Glu  Leu  Met  Val
          115                      120                      125

Leu  Leu  Glu  Cys  Asn  Ile  Pro  Pro  Lys  Asp  Ala  Asp  Gly  Thr  Pro  Val
     130                      135                      140

Ile  Gly  Gly  Asp  Gly  Leu  Phe  Glu  Lys  Lys  Leu  Trp  Gly  Leu  Lys  Val
145                      150                      155                      160

Leu  Gln  Glu  Leu  Ser  His  Trp  Thr  Val  Arg  Ser  Ile  His  Asp  Leu  Arg
                    165                      170                      175

Val  Ile  Ser  Cys  His  Gln  Thr  Gly  Ile  Pro  Ala  His  Gly  Ser  His  Tyr
               180                      185                      190

Ile  Ala  Asn  Asp  Lys  Glu  Met
               195
```

(2) INFORMATION FOR SEQ ID NO:4:

(i) SEQUENCE CHARACTERISTICS:
        (A) LENGTH: 186 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO:4:

```
Met  Ala  Phe  Ala  Glu  Gln  Ser  Pro  Leu  Thr  Leu  His  Arg  Arg  Asp  Leu
1                   5                        10                       15

Cys  Ser  Arg  Ser  Ile  Trp  Leu  Ala  Arg  Lys  Ile  Arg  Ser  Asp  Leu  Thr
               20                       25                  30

Ala  Leu  Met  Glu  Ser  Tyr  Val  Lys  His  Gln  Gly  Leu  Asn  Lys  Asn  Ile
          35                       40                       45

Ser  Leu  Asp  Ser  Val  Asp  Pro  Val  Ala  Ser  Thr  Asp  Arg  Trp  Ser  Glu
     50                       55                       60
```

```
    Met   Thr   Glu   Ala   Glu   Arg   Leu   Gln   Glu   Asn   Leu   Gln   Ala   Tyr   Arg   Gln
    65                      70                            75                            80

Gly   Met   Leu   Thr   Arg   Leu   Leu   Glu   Asp   Gln   Arg   Val   His   Phe   Thr   Pro
                            85                      90                            95

Thr   Glu   Gly   Asp   Phe   His   Gln   Ala   His   Thr   Leu   Thr   Gln   Val   Ser   Ala
                      100                           105                           110

Phe   Ala   Tyr   Gln   Leu   Glu   Glu   Leu   Met   Ala   Leu   Leu   Glu   Gln   Lys   Val
                      115                     120                           125

Asn   Glu   Ala   Asp   Gly   Met   Pro   Val   Thr   Ile   Gly   Asp   Gly   Gly   Leu   Phe
                130                     135                           140

Glu   Lys   Leu   Trp   Gly   Leu   Lys   Val   Leu   Leu   Ser   Gln   Trp   Thr   Val   Arg
    145                           150                           155                           160

Ser   Ile   His   Asp   Leu   Arg   Val   Ile   Ser   Ser   His   His   Met   Gly   Ile   Ser
                            165                           170                           175

Ala   His   Ser   His   Tyr   Gly   Ala   Lys   Gln   Met
                      180                     185
```

( 2 ) INFORMATION FOR SEQ ID NO:5:

( i ) SEQUENCE CHARACTERISTICS:
        ( A ) LENGTH: 195 amino acids
        ( B ) TYPE: amino acid
        ( C ) STRANDEDNESS: single
        ( D ) TOPOLOGY: unknown ( i i ) MOLECULE TYPE: protein ( x i ) SEQUENCE DESCRIPTION: SEQ ID NO:5:

```
    Met   Ala   Ala   Ala   Asp   Thr   Pro   Ser   Ala   Thr   Leu   Arg   His   His   Asp   Leu
    1                       5                             10                            15

Cys   Ser   Arg   Gly   Ile   Arg   Leu   Ala   Arg   Lys   Met   Arg   Ser   Asp   Val   Thr
                      20                            25                            30

Asp   Leu   Leu   Asp   Ile   Tyr   Val   Glu   Arg   Gln   Gly   Leu   Asp   Ala   Ser   Ile
                35                      40                            45

Ser   Val   Ala   Ala   Val   Asp   Gly   Val   Pro   Thr   Ala   Ala   Val   Glu   Arg   Trp
          50                            55                            60

Ala   Glu   Gln   Thr   Gly   Thr   Gln   Arg   Leu   Leu   Asp   Asn   Leu   Ala   Ala   Tyr
    65                      70                            75                            80

Arg   Ala   Phe   Arg   Thr   Leu   Leu   Ala   Gln   Met   Leu   Glu   Glu   Gln   Arg   Glu
                            85                      90                            95

Leu   Leu   Gly   Asp   Thr   Asp   Ala   Glu   Leu   Gly   Pro   Ala   Leu   Ala   Ala   Met
                      100                           105                           110

Leu   Leu   Gln   Val   Ser   Ala   Phe   Val   Tyr   His   Leu   Glu   Glu   Leu   Leu   Glu
                      115                     120                           125

Leu   Glu   Ser   Arg   Gly   Ala   Pro   Ala   Glu   Glu   Gly   Ser   Glu   Pro   Pro   Ala
                130                     135                           140

Pro   Pro   Arg   Leu   Ser   Leu   Phe   Glu   Gln   Lys   Leu   Arg   Gly   Leu   Arg   Val
    145                           150                           155                           160

Leu   Arg   Glu   Leu   Ala   Gln   Trp   Ala   Val   Arg   Ser   Val   Arg   Asp   Leu   Arg
                            165                           170                           175

Gln   Leu   Ser   Lys   His   Gly   Pro   Gly   Ser   Gly   Ala   Ala   Leu   Gly   Leu   Pro
                      180                     185                           190

Glu   Ser   Gln
                195
```

( 2 ) INFORMATION FOR SEQ ID NO:6:

( i ) SEQUENCE CHARACTERISTICS:

(A) LENGTH: 200 amino acids
(B) TYPE: amino acid
(C) STRANDEDNESS: single
(D) TOPOLOGY: unknown (ii) MOLECULE TYPE: protein (xi) SEQUENCE DESCRIPTION: SEQ ID NO:6:

| Met | Ala | Phe | Thr | Glu | His | Ser | Pro | Leu | Thr | Pro | His | Arg | Arg | Asp | Leu |
|---|---|---|---|---|---|---|---|---|---|---|---|---|---|---|---|
| 1 | | | | 5 | | | | | 10 | | | | | | 15 |

| Cys | Ser | Arg | Ser | Ile | Trp | Leu | Ala | Arg | Lys | Ile | Arg | Ser | Asp | Leu | Thr |
|---|---|---|---|---|---|---|---|---|---|---|---|---|---|---|---|
| | | | 20 | | | | | 25 | | | | | 30 | | |

| Ala | Leu | Thr | Glu | Ser | Tyr | Val | Lys | His | Gln | Gly | Leu | Asn | Lys | Asn | Ile |
|---|---|---|---|---|---|---|---|---|---|---|---|---|---|---|---|
| | | | 35 | | | | 40 | | | | | 45 | | | |

| Asn | Leu | Asp | Ser | Val | Asp | Gly | Val | Pro | Val | Ala | Ser | Thr | Asp | Arg | Trp |
|---|---|---|---|---|---|---|---|---|---|---|---|---|---|---|---|
| | 50 | | | | | 55 | | | | | | 60 | | | |

| Ser | Glu | Met | Thr | Glu | Ala | Glu | Arg | Leu | Gln | Glu | Asn | Leu | Gln | Ala | Tyr |
|---|---|---|---|---|---|---|---|---|---|---|---|---|---|---|---|
| 65 | | | | | 70 | | | | | 75 | | | | | 80 |

| Arg | Thr | Phe | Gln | Gly | Met | Leu | Thr | Lys | Leu | Leu | Glu | Asp | Gln | Arg | Val |
|---|---|---|---|---|---|---|---|---|---|---|---|---|---|---|---|
| | | | | 85 | | | | | 90 | | | | | 95 | |

| His | Phe | Thr | Pro | Thr | Glu | Gly | Asp | Phe | His | Gln | Ala | Ile | His | Thr | Leu |
|---|---|---|---|---|---|---|---|---|---|---|---|---|---|---|---|
| | | | 100 | | | | | 105 | | | | | | 110 | |

| Met | Leu | Gln | Val | Ser | Ala | Phe | Ala | Tyr | Gln | Leu | Glu | Glu | Leu | Met | Val |
|---|---|---|---|---|---|---|---|---|---|---|---|---|---|---|---|
| | | 115 | | | | | 120 | | | | | | 125 | | |

| Leu | Leu | Glu | Gln | Lys | Ile | Pro | Glu | Asn | Glu | Ala | Asp | Gly | Met | Pro | Ala |
|---|---|---|---|---|---|---|---|---|---|---|---|---|---|---|---|
| | 130 | | | | | 135 | | | | | 140 | | | | |

| Thr | Val | Gly | Asp | Gly | Gly | Leu | Phe | Glu | Lys | Lys | Leu | Trp | Gly | Leu | Lys |
|---|---|---|---|---|---|---|---|---|---|---|---|---|---|---|---|
| 145 | | | | | 150 | | | | | 155 | | | | | 160 |

| Val | Leu | Gln | Glu | Leu | Ser | Gln | Trp | Thr | Val | Arg | Ser | Ile | His | Asp | Leu |
|---|---|---|---|---|---|---|---|---|---|---|---|---|---|---|---|
| | | | | 165 | | | | | 170 | | | | | 175 | |

| Arg | Val | Ile | Ser | Ser | His | Gln | Met | Gly | Ile | Ser | Ala | Leu | Glu | Ser | His |
|---|---|---|---|---|---|---|---|---|---|---|---|---|---|---|---|
| | | | 180 | | | | | 185 | | | | | 190 | | |

| Tyr | Gly | Ala | Lys | Asp | Lys | Gln | Met |
|---|---|---|---|---|---|---|---|
| | | 195 | | | | | 200 |

(2) INFORMATION FOR SEQ ID NO:7:

(i) SEQUENCE CHARACTERISTICS:
(A) LENGTH: 200 amino acids
(B) TYPE: amino acid
(C) STRANDEDNESS: single
(D) TOPOLOGY: unknown (ii) MOLECULE TYPE: protein (xi) SEQUENCE DESCRIPTION: SEQ ID NO:7:

| Met | Ala | Phe | Ala | Glu | Gln | Thr | Pro | Leu | Thr | Leu | His | Arg | Arg | Asp | Leu |
|---|---|---|---|---|---|---|---|---|---|---|---|---|---|---|---|
| 1 | | | | 5 | | | | | 10 | | | | | | 15 |

| Cys | Ser | Arg | Ser | Ile | Trp | Leu | Ala | Arg | Lys | Ile | Arg | Ser | Asp | Leu | Thr |
|---|---|---|---|---|---|---|---|---|---|---|---|---|---|---|---|
| | | | 20 | | | | | 25 | | | | | 30 | | |

| Ala | Leu | Met | Glu | Ser | Tyr | Val | Lys | His | Gln | Gly | Leu | Asn | Lys | Asn | Ile |
|---|---|---|---|---|---|---|---|---|---|---|---|---|---|---|---|
| | | | 35 | | | | 40 | | | | | 45 | | | |

| Asn | Leu | Asp | Ser | Ala | Asp | Gly | Met | Pro | Val | Ala | Ser | Thr | Asp | Gln | Trp |
|---|---|---|---|---|---|---|---|---|---|---|---|---|---|---|---|
| | 50 | | | | | 55 | | | | | | 60 | | | |

| Ser | Glu | Leu | Thr | Glu | Ala | Glu | Arg | Leu | Gln | Glu | Asn | Leu | Gln | Ala | Tyr |
|---|---|---|---|---|---|---|---|---|---|---|---|---|---|---|---|
| 65 | | | | | 70 | | | | | 75 | | | | | 80 |

| Arg | Thr | Phe | His | Val | Leu | Leu | Ala | Arg | Leu | Leu | Glu | Asp | Gln | Gln | Val |
|---|---|---|---|---|---|---|---|---|---|---|---|---|---|---|---|
| | | | | 85 | | | | | 90 | | | | | 95 | |

| His | Phe | Thr | Pro | Thr | Glu | Gly | Asp | Phe | His | Gln | Ala | Ile | His | Thr | Leu |

|     |     |     |     |     | 100 |     |     |     | 105 |     |     |     | 110 |     |
| --- | --- | --- | --- | --- | --- | --- | --- | --- | --- | --- | --- | --- | --- | --- |
| Leu | Leu | Gln | Val | Ala | Ala | Phe | Ala | Tyr | Gln | Ile | Glu | Glu | Leu | Met | Ile |
|     |     | 115 |     |     |     |     | 120 |     |     |     | 125 |     |     |     |
| Leu | Leu | Glu | Tyr | Lys | Ile | Pro | Arg | Asn | Glu | Ala | Asp | Gly | Met | Pro | Ile |
|     | 130 |     |     |     | 135 |     |     |     |     | 140 |     |     |     |     |
| Asn | Val | Gly | Asp | Gly | Gly | Leu | Phe | Glu | Lys | Lys | Leu | Trp | Gly | Leu | Lys |
| 145 |     |     |     |     | 150 |     |     |     |     | 155 |     |     |     |     | 160 |
| Val | Leu | Gln | Glu | Leu | Ser | Gln | Trp | Thr | Val | Arg | Ser | Ile | His | Asp | Leu |
|     |     |     |     | 165 |     |     |     |     | 170 |     |     |     |     | 175 |     |
| Arg | Phe | Ile | Ser | Ser | His | Gln | Thr | Gly | Ile | Pro | Ala | Arg | Gly | Ser | His |
|     |     |     | 180 |     |     |     |     | 185 |     |     |     |     | 190 |     |     |
| Tyr | Ile | Ala | Asn | Asn | Lys | Lys | Met |
|     |     |     | 195 |     |     |     | 200 |

( 2 ) INFORMATION FOR SEQ ID NO:8:

( i ) SEQUENCE CHARACTERISTICS:
        ( A ) LENGTH: 200 amino acids
        ( B ) TYPE: amino acid
        ( C ) STRANDEDNESS: single
        ( D ) TOPOLOGY: unknown ( i i ) MOLECULE TYPE: protein ( x i ) SEQUENCE DESCRIPTION: SEQ ID NO:8:

| Met | Ala | Phe | Thr | Glu | His | Ser | Pro | Leu | Thr | Pro | His | Arg | Arg | Asp | Leu |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |
| Cys | Ser | Arg | Ser | Ile | Trp | Leu | Ala | Arg | Lys | Ile | Arg | Ser | Asp | Leu | Thr |
|     |     |     | 20  |     |     |     |     | 25  |     |     |     |     | 30  |     |     |
| Ala | Leu | Thr | Glu | Ser | Tyr | Val | Lys | His | Gln | Gly | Leu | Asn | Lys | Asn | Ile |
|     |     | 35  |     |     |     |     | 40  |     |     |     |     | 45  |     |     |     |
| Asn | Leu | Asp | Ser | Ala | Asp | Gly | Met | Pro | Val | Ala | Ser | Thr | Asp | Gln | Trp |
|     | 50  |     |     |     |     | 55  |     |     |     |     | 60  |     |     |     |     |
| Ser | Glu | Leu | Thr | Glu | Ala | Glu | Arg | Leu | Gln | Glu | Asn | Leu | Gln | Ala | Tyr |
| 65  |     |     |     |     | 70  |     |     |     |     | 75  |     |     |     |     | 80  |
| Arg | Thr | Phe | His | Val | Leu | Leu | Ala | Arg | Leu | Leu | Glu | Asp | Gln | Gln | Val |
|     |     |     |     | 85  |     |     |     |     | 90  |     |     |     |     | 95  |     |
| His | Phe | Thr | Pro | Thr | Glu | Gly | Asp | Phe | His | Gln | Ala | Ile | His | Thr | Leu |
|     |     |     | 100 |     |     |     |     | 105 |     |     |     |     | 110 |     |     |
| Leu | Leu | Gln | Val | Ala | Ala | Phe | Ala | Tyr | Gln | Ile | Glu | Glu | Leu | Met | Ile |
|     |     | 115 |     |     |     |     | 120 |     |     |     | 125 |     |     |     |     |
| Leu | Leu | Glu | Tyr | Lys | Ile | Pro | Arg | Asn | Glu | Ala | Asp | Gly | Met | Pro | Ile |
|     | 130 |     |     |     | 135 |     |     |     |     | 140 |     |     |     |     |     |
| Asn | Val | Gly | Asp | Gly | Gly | Leu | Phe | Glu | Lys | Lys | Leu | Trp | Gly | Leu | Lys |
| 145 |     |     |     |     | 150 |     |     |     |     | 155 |     |     |     |     | 160 |
| Val | Leu | Gln | Glu | Leu | Ser | Gln | Trp | Thr | Val | Arg | Ser | Ile | His | Asp | Leu |
|     |     |     |     | 165 |     |     |     |     | 170 |     |     |     |     | 175 |     |
| Arg | Val | Ile | Ser | Ser | His | Gln | Met | Gly | Ile | Ser | Ala | Leu | Glu | Ser | His |
|     |     |     | 180 |     |     |     |     | 185 |     |     |     |     | 190 |     |     |
| Tyr | Gly | Ala | Lys | Asp | Lys | Gln | Met |
|     |     |     | 195 |     |     |     | 200 |

( 2 ) INFORMATION FOR SEQ ID NO:9:

( i ) SEQUENCE CHARACTERISTICS:
        ( A ) LENGTH: 200 amino acids
        ( B ) TYPE: amino acid
        ( C ) STRANDEDNESS: single
        ( D ) TOPOLOGY: unknown ( i i ) MOLECULE TYPE: protein ( x i ) SEQUENCE DESCRIPTION: SEQ ID NO:9:

| Met | Ala | Phe | Ala | Glu | Gln | Thr | Pro | Leu | Thr | Leu | His | Arg | Arg | Asp | Leu |
| 1 | | | | 5 | | | | | 10 | | | | | 15 | |

| Cys | Ser | Arg | Ser | Ile | Trp | Leu | Ala | Arg | Lys | Ile | Arg | Ser | Asp | Leu | Thr |
| | | | 20 | | | | | 25 | | | | | 30 | | |

| Ala | Leu | Met | Glu | Ser | Tyr | Val | Lys | His | Gln | Gly | Leu | Asn | Lys | Asn | Ile |
| | | 35 | | | | | 40 | | | | | 45 | | | |

| Asn | Leu | Asp | Ser | Val | Asp | Gly | Val | Pro | Val | Ala | Ser | Thr | Asp | Arg | Trp |
| | 50 | | | | | 55 | | | | | 60 | | | | |

| Ser | Glu | Met | Thr | Glu | Ala | Glu | Arg | Leu | Gln | Glu | Asn | Leu | Gln | Ala | Tyr |
| 65 | | | | | 70 | | | | | 75 | | | | | 80 |

| Arg | Thr | Phe | Gln | Gly | Met | Leu | Thr | Lys | Leu | Leu | Glu | Asp | Gln | Arg | Val |
| | | | | 85 | | | | | 90 | | | | | 95 | |

| His | Phe | Thr | Pro | Thr | Glu | Gly | Asp | Phe | His | Gln | Ala | Ile | His | Thr | Leu |
| | | | 100 | | | | | 105 | | | | | 110 | | |

| Met | Leu | Gln | Val | Ser | Ala | Phe | Ala | Tyr | Gln | Leu | Glu | Glu | Leu | Met | Val |
| | | | 115 | | | | | 120 | | | | | 125 | | |

| Leu | Leu | Glu | Gln | Lys | Ile | Pro | Glu | Asn | Glu | Ala | Asp | Gly | Met | Pro | Ala |
| | | 130 | | | | | 135 | | | | | 140 | | | |

| Thr | Val | Gly | Asp | Gly | Gly | Leu | Phe | Glu | Lys | Lys | Leu | Trp | Gly | Leu | Lys |
| 145 | | | | | 150 | | | | | 155 | | | | | 160 |

| Val | Leu | Gln | Glu | Leu | Ser | Gln | Trp | Thr | Val | Arg | Ser | Ile | His | Asp | Leu |
| | | | | 165 | | | | | 170 | | | | | 175 | |

| Arg | Phe | Ile | Ser | Ser | His | Gln | Thr | Gly | Ile | Pro | Ala | Arg | Gly | Ser | His |
| | | | 180 | | | | | 185 | | | | | 190 | | |

| Tyr | Ile | Ala | Asn | Asn | Lys | Lys | Met |
| | | 195 | | | | | 200 |

( 2 ) INFORMATION FOR SEQ ID NO:10:

( i ) SEQUENCE CHARACTERISTICS:
        ( A ) LENGTH: 200 amino acids
        ( B ) TYPE: amino acid
        ( C ) STRANDEDNESS: single
        ( D ) TOPOLOGY: unknown ( i i ) MOLECULE TYPE: protein ( x i ) SEQUENCE DESCRIPTION: SEQ ID NO:10:

| Met | Ala | Phe | Thr | Glu | His | Ser | Pro | Leu | Thr | Pro | His | Arg | Arg | Asp | Leu |
| 1 | | | | 5 | | | | | 10 | | | | | 15 | |

| Cys | Ser | Arg | Ser | Ile | Trp | Leu | Ala | Arg | Lys | Ile | Arg | Ser | Asp | Leu | Thr |
| | | | 20 | | | | | 25 | | | | | 30 | | |

| Ala | Leu | Thr | Glu | Ser | Tyr | Val | Lys | His | Gln | Gly | Leu | Asn | Lys | Asn | Ile |
| | | 35 | | | | | 40 | | | | | 45 | | | |

| Asn | Leu | Asp | Ser | Ala | Asp | Gly | Met | Pro | Val | Ala | Ser | Thr | Asp | Gln | Trp |
| | 50 | | | | | 55 | | | | | 60 | | | | |

| Ser | Glu | Leu | Thr | Glu | Ala | Glu | Arg | Leu | Gln | Glu | Asn | Leu | Gln | Ala | Tyr |
| 65 | | | | | 70 | | | | | 75 | | | | | 80 |

| Arg | Thr | Phe | Gln | Gly | Met | Leu | Thr | Lys | Leu | Leu | Glu | Asp | Gln | Arg | Val |
| | | | | 85 | | | | | 90 | | | | | 95 | |

| His | Phe | Thr | Pro | Thr | Glu | Gly | Asp | Phe | His | Gln | Ala | Ile | His | Thr | Leu |
| | | | 100 | | | | | 105 | | | | | 110 | | |

| Met | Leu | Gln | Val | Ser | Ala | Phe | Ala | Tyr | Gln | Leu | Glu | Glu | Leu | Met | Val |
| | | | 115 | | | | | 120 | | | | | 125 | | |

|     |     |     |     |     |     |     |     |     |     |     |     |     |     |     |     |
| --- | --- | --- | --- | --- | --- | --- | --- | --- | --- | --- | --- | --- | --- | --- | --- |
| Leu | Leu | Glu | Gln | Lys | Ile | Pro | Glu | Asn | Glu | Ala | Asp | Gly | Met | Pro | Ala |
|     | 130 |     |     |     |     | 135 |     |     |     |     | 140 |     |     |     |     |
| Thr | Val | Gly | Asp | Gly | Gly | Leu | Phe | Glu | Lys | Lys | Leu | Trp | Gly | Leu | Lys |
| 145 |     |     |     |     | 150 |     |     |     |     | 155 |     |     |     |     | 160 |
| Val | Leu | Gln | Glu | Leu | Ser | Gln | Trp | Thr | Val | Arg | Ser | Ile | His | Asp | Leu |
|     |     |     |     | 165 |     |     |     | 170 |     |     |     |     | 175 |     |     |
| Arg | Phe | Ile | Ser | Ser | His | Gln | Thr | Gly | Ile | Pro | Ala | Arg | Gly | Ser | His |
|     |     |     | 180 |     |     |     |     | 185 |     |     |     |     | 190 |     |     |
| Tyr | Ile | Ala | Asn | Asn | Lys | Lys | Met |     |     |     |     |     |     |     |     |
|     |     | 195 |     |     |     |     | 200 |     |     |     |     |     |     |     |     |

( 2 ) INFORMATION FOR SEQ ID NO:11:

( i ) SEQUENCE CHARACTERISTICS:
        ( A ) LENGTH: 200 amino acids
        ( B ) TYPE: amino acid
        ( C ) STRANDEDNESS: single
        ( D ) TOPOLOGY: unknown ( i i ) MOLECULE TYPE: protein ( x i ) SEQUENCE DESCRIPTION: SEQ ID NO:11:

|     |     |     |     |     |     |     |     |     |     |     |     |     |     |     |     |
| --- | --- | --- | --- | --- | --- | --- | --- | --- | --- | --- | --- | --- | --- | --- | --- |
| Met | Ala | Phe | Thr | Glu | His | Ser | Pro | Leu | Thr | Pro | His | Arg | Arg | Asp | Leu |
| 1   |     |     |     | 5   |     |     |     |     | 10  |     |     |     |     | 15  |     |
| Cys | Ser | Arg | Ser | Ile | Trp | Leu | Ala | Arg | Lys | Ile | Arg | Ser | Asp | Leu | Thr |
|     |     |     | 20  |     |     |     |     | 25  |     |     |     |     | 30  |     |     |
| Ala | Leu | Met | Glu | Ser | Tyr | Val | Lys | His | Gln | Gly | Leu | Asn | Lys | Asn | Ile |
|     |     | 35  |     |     |     |     | 40  |     |     |     |     | 45  |     |     |     |
| Asn | Leu | Asp | Ser | Val | Asp | Gly | Val | Pro | Val | Ala | Ser | Thr | Asp | Arg | Trp |
|     | 50  |     |     |     |     | 55  |     |     |     |     | 60  |     |     |     |     |
| Ser | Glu | Met | Thr | Glu | Ala | Glu | Arg | Leu | Gln | Glu | Asn | Leu | Gln | Ala | Tyr |
| 65  |     |     |     |     | 70  |     |     |     |     | 75  |     |     |     |     | 80  |
| Arg | Thr | Phe | His | Val | Leu | Leu | Ala | Arg | Leu | Leu | Glu | Asp | Gln | Gln | Val |
|     |     |     |     | 85  |     |     |     |     | 90  |     |     |     |     | 95  |     |
| His | Phe | Thr | Pro | Thr | Glu | Gly | Asp | Phe | His | Gln | Ala | Ile | His | Thr | Leu |
|     |     |     | 100 |     |     |     |     | 105 |     |     |     |     | 110 |     |     |
| Leu | Leu | Gln | Val | Ala | Ala | Phe | Ala | Tyr | Gln | Ile | Glu | Glu | Leu | Met | Ile |
|     |     | 115 |     |     |     |     | 120 |     |     |     |     | 125 |     |     |     |
| Leu | Leu | Glu | Tyr | Lys | Ile | Pro | Arg | Asn | Glu | Ala | Asp | Gly | Met | Pro | Ile |
|     | 130 |     |     |     |     | 135 |     |     |     |     | 140 |     |     |     |     |
| Asn | Val | Gly | Asp | Gly | Gly | Leu | Phe | Glu | Lys | Lys | Leu | Trp | Gly | Leu | Lys |
| 145 |     |     |     |     | 150 |     |     |     |     | 155 |     |     |     |     | 160 |
| Val | Leu | Gln | Glu | Leu | Ser | Gln | Trp | Thr | Val | Arg | Ser | Ile | His | Asp | Leu |
|     |     |     |     | 165 |     |     |     | 170 |     |     |     |     | 175 |     |     |
| Arg | Phe | Ile | Ser | Ser | His | Gln | Thr | Gly | Ile | Pro | Ala | Arg | Gly | Ser | His |
|     |     |     | 180 |     |     |     |     | 185 |     |     |     |     | 190 |     |     |
| Tyr | Ile | Ala | Asn | Asn | Lys | Lys | Met |     |     |     |     |     |     |     |     |
|     |     | 195 |     |     |     |     | 200 |     |     |     |     |     |     |     |     |

( 2 ) INFORMATION FOR SEQ ID NO:12:

( i ) SEQUENCE CHARACTERISTICS:
        ( A ) LENGTH: 200 amino acids
        ( B ) TYPE: amino acid
        ( C ) STRANDEDNESS: single
        ( D ) TOPOLOGY: unknown ( i i ) MOLECULE TYPE: protein ( x i ) SEQUENCE DESCRIPTION: SEQ ID NO:12:

```
Met  Ala  Phe  Thr  Glu  His  Ser  Pro  Leu  Thr  Pro  His  Arg  Arg  Asp  Leu
1              5                        10                       15

Cys  Ser  Arg  Ser  Ile  Trp  Leu  Ala  Arg  Lys  Ile  Arg  Ser  Asp  Leu  Thr
               20                       25                  30

Ala  Leu  Thr  Glu  Ser  Tyr  Val  Lys  His  Gln  Gly  Leu  Asn  Lys  Asn  Ile
          35                       40                       45

Asn  Leu  Asp  Ser  Val  Asp  Gly  Val  Pro  Val  Ala  Ser  Thr  Asp  Arg  Trp
     50                       55                       60

Ser  Glu  Met  Thr  Glu  Ala  Glu  Arg  Leu  Gln  Glu  Asn  Leu  Gln  Ala  Tyr
65                       70                       75                       80

Arg  Thr  Phe  His  Val  Leu  Leu  Ala  Arg  Leu  Leu  Glu  Asp  Gln  Gln  Val
                    85                       90                       95

His  Phe  Thr  Pro  Thr  Glu  Gly  Asp  Phe  His  Gln  Ala  Ile  His  Thr  Leu
               100                      105                      110

Leu  Leu  Gln  Val  Ala  Ala  Phe  Ala  Tyr  Gln  Ile  Glu  Glu  Leu  Met  Ile
          115                      120                      125

Leu  Leu  Glu  Tyr  Lys  Ile  Pro  Arg  Asn  Glu  Ala  Asp  Gly  Met  Pro  Ile
     130                      135                      140

Asn  Val  Gly  Asp  Gly  Gly  Leu  Phe  Glu  Lys  Lys  Leu  Trp  Gly  Leu  Lys
145                      150                      155                      160

Val  Leu  Gln  Glu  Leu  Ser  Gln  Trp  Thr  Val  Arg  Ser  Ile  His  Asp  Leu
                    165                      170                      175

Arg  Phe  Ile  Ser  Ser  His  Gln  Thr  Gly  Ile  Pro  Ala  Arg  Gly  Ser  His
               180                      185                      190

Tyr  Ile  Ala  Asn  Asn  Lys  Lys  Met
          195                      200
```

( 2 ) INFORMATION FOR SEQ ID NO:13:

( i ) SEQUENCE CHARACTERISTICS:
        ( A ) LENGTH: 200 amino acids
        ( B ) TYPE: amino acid
        ( C ) STRANDEDNESS: single
        ( D ) TOPOLOGY: unknown ( i i ) MOLECULE TYPE: protein ( x i ) SEQUENCE DESCRIPTION: SEQ ID NO:13:

```
Met  Ala  Phe  Thr  Glu  His  Ser  Pro  Leu  Thr  Pro  His  Arg  Arg  Asp  Leu
1              5                        10                       15

Cys  Ser  Arg  Ser  Ile  Trp  Leu  Ala  Arg  Lys  Ile  Arg  Ser  Asp  Leu  Thr
               20                       25                  30

Ala  Leu  Thr  Glu  Ser  Tyr  Val  Lys  His  Gln  Gly  Leu  Asn  Lys  Asn  Ile
          35                       40                       45

Asn  Leu  Asp  Ser  Val  Asp  Gly  Met  Pro  Val  Ala  Ser  Thr  Asp  Gln  Trp
     50                       55                       60

Ser  Glu  Met  Thr  Glu  Ala  Glu  Arg  Leu  Gln  Glu  Asn  Leu  Gln  Ala  Tyr
65                       70                       75                       80

Arg  Thr  Phe  His  Val  Leu  Leu  Ala  Arg  Leu  Leu  Glu  Asp  Gln  Gln  Val
                    85                       90                       95

His  Phe  Thr  Pro  Thr  Glu  Gly  Asp  Phe  His  Gln  Ala  Ile  His  Thr  Leu
               100                      105                      110

Leu  Leu  Gln  Val  Ala  Ala  Phe  Ala  Tyr  Gln  Ile  Glu  Glu  Leu  Met  Ile
          115                      120                      125

Leu  Leu  Glu  Tyr  Lys  Ile  Pro  Arg  Asn  Glu  Ala  Asp  Gly  Met  Pro  Ile
     130                      135                      140
```

-continued

```
Asn Val Gly Asp Gly Gly Leu Phe Glu Lys Lys Leu Trp Gly Leu Lys
145                 150                 155                 160

Val Leu Gln Glu Leu Ser Gln Trp Thr Val Arg Ser Ile His Asp Leu
                165                 170                 175

Arg Phe Ile Ser Ser His Gln Thr Gly Ile Pro Ala Arg Gly Ser His
            180                 185                 190

Tyr Ile Ala Asn Asn Lys Lys Met
        195                 200
```

(2) INFORMATION FOR SEQ ID NO:14:

(i) SEQUENCE CHARACTERISTICS:
    (A) LENGTH: 200 amino acids
    (B) TYPE: amino acid
    (C) STRANDEDNESS: single
    (D) TOPOLOGY: unknown (ii) MOLECULE TYPE: protein (xi) SEQUENCE DESCRIPTION: SEQ ID NO:14:

```
Met Ala Phe Thr Glu His Ser Pro Leu Thr Pro His Arg Arg Asp Leu
1               5                   10                  15

Cys Ser Arg Ser Ile Trp Leu Ala Arg Lys Ile Arg Ser Asp Leu Thr
                20                  25                  30

Ala Leu Thr Glu Ser Tyr Val Lys His Gln Gly Leu Asn Lys Asn Ile
            35                  40                  45

Asn Leu Asp Ser Val Asp Gly Val Pro Val Ala Ser Thr Asp Gln Trp
        50                  55                  60

Ser Glu Leu Thr Glu Ala Glu Arg Leu Gln Glu Asn Leu Gln Ala Tyr
65                  70                  75                  80

Arg Thr Phe His Val Leu Leu Ala Arg Leu Leu Glu Asp Gln Gln Val
                85                  90                  95

His Phe Thr Pro Thr Glu Gly Asp Phe His Gln Ala Ile His Thr Leu
                100                 105                 110

Leu Leu Gln Val Ala Ala Phe Ala Tyr Gln Ile Glu Glu Leu Met Ile
            115                 120                 125

Leu Leu Glu Tyr Lys Ile Pro Arg Asn Glu Ala Asp Gly Met Pro Ile
        130                 135                 140

Asn Val Gly Asp Gly Gly Leu Phe Glu Lys Lys Leu Trp Gly Leu Lys
145                 150                 155                 160

Val Leu Gln Glu Leu Ser Gln Trp Thr Val Arg Ser Ile His Asp Leu
                165                 170                 175

Arg Phe Ile Ser Ser His Gln Thr Gly Ile Pro Ala Arg Gly Ser His
            180                 185                 190

Tyr Ile Ala Asn Asn Lys Lys Met
        195                 200
```

(2) INFORMATION FOR SEQ ID NO:15:

(i) SEQUENCE CHARACTERISTICS:
    (A) LENGTH: 200 amino acids
    (B) TYPE: amino acid
    (C) STRANDEDNESS: single
    (D) TOPOLOGY: unknown (ii) MOLECULE TYPE: protein (xi) SEQUENCE DESCRIPTION: SEQ ID NO:15:

```
Met Ala Phe Thr Glu His Ser Pro Leu Thr Pro His Arg Arg Asp Leu
1               5                   10                  15
```

|     |     |     |     |     |     |     |     |     |     |     |     |     |     |     |
| --- | --- | --- | --- | --- | --- | --- | --- | --- | --- | --- | --- | --- | --- | --- |
| Cys | Ser | Arg | Ser<br>20 | Ile | Trp | Leu | Ala | Arg<br>25 | Lys | Ile | Arg | Ser | Asp<br>30 | Leu | Thr |
| Ala | Leu | Thr<br>35 | Glu | Ser | Tyr | Val | Lys<br>40 | His | Gln | Gly | Leu | Asn<br>45 | Lys | Asn | Ile |
| Asn | Leu<br>50 | Asp | Ser | Ala | Asp | Gly<br>55 | Met | Pro | Val | Ala | Ser<br>60 | Thr | Asp | Arg | Trp |
| Ser<br>65 | Glu | Leu | Thr | Glu | Ala<br>70 | Glu | Arg | Leu | Gln | Glu<br>75 | Asn | Leu | Gln | Ala | Tyr<br>80 |
| Arg | Thr | Phe | His | Val<br>85 | Leu | Leu | Ala | Arg | Leu<br>90 | Leu | Glu | Asp | Gln | Val<br>95 |
| His | Phe | Thr | Pro<br>100 | Thr | Glu | Gly | Asp | Phe<br>105 | His | Gln | Ala | Ile | His<br>110 | Thr | Leu |
| Leu | Leu | Gln<br>115 | Val | Ala | Ala | Phe | Ala<br>120 | Tyr | Gln | Ile | Glu | Glu<br>125 | Leu | Met | Ile |
| Leu | Leu<br>130 | Glu | Tyr | Lys | Ile | Pro<br>135 | Arg | Asn | Glu | Ala | Asp<br>140 | Gly | Met | Pro | Ile |
| Asn<br>145 | Val | Gly | Asp | Gly | Gly<br>150 | Leu | Phe | Glu | Lys | Lys<br>155 | Leu | Trp | Gly | Leu | Lys<br>160 |
| Val | Leu | Gln | Glu | Leu<br>165 | Ser | Gln | Trp | Thr | Val<br>170 | Arg | Ser | Ile | His | Asp<br>175 | Leu |
| Arg | Phe | Ile | Ser<br>180 | Ser | His | Gln | Thr | Gly<br>185 | Ile | Pro | Ala | Arg | Gly<br>190 | Ser | His |
| Tyr | Ile | Ala<br>195 | Asn | Asn | Lys | Lys | Met<br>200 |

( 2 ) INFORMATION FOR SEQ ID NO:16:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

ACGGTAAGCT TGGAGGTTCT C                                                21

( 2 ) INFORMATION FOR SEQ ID NO:17:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

TCTATCTGGC TAGCAAGGAA GATTCGTTCA GACCTGACTG CTCTTACG        48

( 2 ) INFORMATION FOR SEQ ID NO:18:

( i ) SEQUENCE CHARACTERISTICS:
        ( A ) LENGTH: 69 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

AAGGTACGAT AAGCTTGGAG GTTCTCTTGG AGTCGCTCTG CCTCAGTCAG CTCACTCCAA        60

CGATCAGTG 69

(2) INFORMATION FOR SEQ ID NO:19:

(i) SEQUENCE CHARACTERISTICS:
        (A) LENGTH: 21 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO:19:

TCTATCTGGC TAGCAAGGAA G 21

(2) INFORMATION FOR SEQ ID NO:20:

(i) SEQUENCE CHARACTERISTICS:
        (A) LENGTH: 782 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: Coding Sequence
        (B) LOCATION: 126...725
        (D) OTHER INFORMATION:
        (A) NAME/KEY: Human CNTF
        (B) LOCATION: 1...782
        (D) OTHER INFORMATION:

(xi) SEQUENCE DESCRIPTION: SEQ ID NO:20:

```
GTGCACAATC  CCATTAGTAG  AGAATGCCAG  TGGGTTTAGT  CTTTGAGAGT  CACATCTCTT      60

ATTTGGACCA  GTATAGACAG  AAGTAAACCC  AGCTGACTTG  TTTCCTGGGA  CAGTTGAGTT     120

AAGGG ATG GCT TTC ACA GAG CAT TCA CCG CTG ACC CCT CAC CGT CGG GAC         170
      Met Ala Phe Thr Glu His Ser Pro Leu Thr Pro His Arg Arg Asp
       1               5                  10                  15

CTC TGT AGC CGC TCT ATC TGG CTA GCA AGG AAG ATT CGT TCA GAC CTG           218
Leu Cys Ser Arg Ser Ile Trp Leu Ala Arg Lys Ile Arg Ser Asp Leu
                 20                  25                  30

ACT GCT CTT ACG GAA TCC TAT GTG AAG CAT CAG GGC CTG AAC AAG AAC           266
Thr Ala Leu Thr Glu Ser Tyr Val Lys His Gln Gly Leu Asn Lys Asn
             35                  40                  45

ATC AAC CTG GAC TCT GCG GAT GGG ATG CCA GTG GCA AGC ACT GAT CAG           314
Ile Asn Leu Asp Ser Ala Asp Gly Met Pro Val Ala Ser Thr Asp Gln
         50                  55                  60

TGG AGT GAG CTG ACC GAG GCA GAG CGA CTC CAA GAG AAC CTT CAA GCT           362
Trp Ser Glu Leu Thr Glu Ala Glu Arg Leu Gln Glu Asn Leu Gln Ala
 65                  70                  75

TAT CGT ACC TTC CAT GTT TTG TTG GCC AGG CTC TTA GAA GAC CAG CAG           410
Tyr Arg Thr Phe His Val Leu Leu Ala Arg Leu Leu Glu Asp Gln Gln
 80                  85                  90                  95

GTG CAT TTT ACC CCA ACC GAA GGT GAC TTC CAT CAA GCT ATA CAT ACC           458
Val His Phe Thr Pro Thr Glu Gly Asp Phe His Gln Ala Ile His Thr
                100                 105                 110

CTT CTT CTC CAA GTC GCT GCC TTT GCA TAC CAG ATA GAG GAG TTA ATG           506
Leu Leu Leu Gln Val Ala Ala Phe Ala Tyr Gln Ile Glu Glu Leu Met
            115                 120                 125

ATA CTC CTG GAA TAC AAG ATC CCC CGC AAT GAG GCT GAT GGG ATG CCT           554
Ile Leu Leu Glu Tyr Lys Ile Pro Arg Asn Glu Ala Asp Gly Met Pro
        130                 135                 140

ATT AAT GTT GGA GAT GGT GGT CTC TTT GAG AAG AAG CTG TGG GGC CTA           602
```

```
Ile  Asn  Val  Gly  Asp  Gly  Gly  Leu  Phe  Glu  Lys  L

5. Modified human ciliary neurotrophic factor comprising human ciliary neurotrophic factor having the modifications Gln63→Arg, Cys17→Ala and a deletion of the C-terminal 13 amino acid residues.

6. The modified ciliary neurotrophic factor of claim 5, designated RG 297.

7. A composition comprising a substantially pure modified ciliary neurotrophic factor according to claim 6 and a carrier.

8. The modified human ciliary neurotrophic factor of claim 5, having the additional modification Trp64→Ala.

9. A composition comprising a substantially pure modified ciliary neurotrophic factor according to claim 8 and a carrier.

10. A composition comprising a substantially pure modified ciliary neurotrophic factor according to claim 5 and a carrier.

11. Modified human ciliary neurotrophic factor comprising human ciliary neurotrophic factor having the modifications Gln63→Arg and a deletion of the C-terminal 13 amino acid residues.

12. The modified ciliary neurotrophic factor of claim 11, designated RG 290.

13. A composition comprising a substantially pure modified ciliary neurotrophic factor according to claim 12 and a carrier.

14. A composition comprising a substantially pure modified ciliary neurotrophic factor according to claim 11 and a carrier.

* * * * *